(12) United States Patent
Solano et al.

(10) Patent No.: US 8,586,058 B2
(45) Date of Patent: Nov. 19, 2013

(54) METHOD FOR PRODUCING MULTIPLE MODIFICATIONS IN THE CHROMOSOME OF GRAM-NEGATIVE BACTERIA AND SALMONELLA STRAINS WHICH ARE DEFICIENT IN C-DI-GMP SYNTHESIS OBTAINED BY SAID METHOD

(75) Inventors: Cristina Solano, Navarra (ES); Begoña García, Navarra (ES); Alejandro Toledo-Arana, Navarra (ES); Cristina Latasa, Navarra (ES); Violeta Zorraquino, Navarra (ES); Jaione Valle, Navarra (ES); Iñigo Lasa, Navarra (ES)

(73) Assignees: Universidad Publica de Navarra, Navarra (ES); Consejo Superior de Investigaciones Cientificas, Madrid (ES)

( * ) Notice: Subject to any disclaimer, the term of this patent is extended or adjusted under 35 U.S.C. 154(b) by 492 days.

(21) Appl. No.: 12/800,809

(22) Filed: May 21, 2010

(65) Prior Publication Data

US 2011/0262480 A1    Oct. 27, 2011

Related U.S. Application Data

(63) Continuation-in-part of application No. PCT/ES2008/070211, filed on Nov. 20, 2008.

(30) Foreign Application Priority Data

Nov. 21, 2007   (ES) .................................. 200703068

(51) Int. Cl.
  *A61K 39/112*   (2006.01)
(52) U.S. Cl.
  USPC ...................... 424/258.1; 435/243; 435/252.1
(58) Field of Classification Search
  None
  See application file for complete search history.

(56) References Cited

PUBLICATIONS

Link AJ et al. Methods for Generating Precise 1-25,50-51 Deletions and Insertions in the Genome of Wild-Type *Escherichia coli*: Application to Open Reading Frame Characterization.Journal of Bacteriology. Nov. 1997, vol. 179(20), pp. 6228-6237. Especially, p. 6228, abstract; p. 6229, col. 2; p. 6230, Fig 1.

Arnaud M et al. New Vector for Efficient Allelic 1-25,50-51 Replacement in Naturally Nontransformable, Low-GC-Content, Gram-Positive Bacteria. Applied and Environmental Microbiology. Nov. 2004, vol. 70(11), pp. 6887-6891. Especially, p. 6887, abstract; p. 6888, cols. 1-2; p. 6889, Fig 1; p. 6889, Fig 2.

Garcia B et al. Role of the GGDEF protein family in Salmonel the cellulose biosynthesis and biofilm formation. Molecular Microbiology. 2004, vol. 54(1), pp. 264-277. Especially, p. 264, col. 1—p. 266, col. 2; p. 268, col. 2—p. 271, col. 1; p. 274, Tab the 2.

Kader A et al. Hierarchical involvement of various GGDEF domain proteins in rdar morphotype development of Salmonel the enteric a serovar Typhimurium. Molecular Microbiology. 2006, vol. 60(3), pp. 602-616. Especially, p. 602, col. 1; p. 605, col. 1—p. 607, col. 2; p. 610, col. 2—p. 611, col. 2.

Simm R et al. Role of EAL-containing proteins in multicellular behavior of Salmonel the enterica serovar Typhimurium. Journal of Bacteriology. May 2007, vol. 189(9), pp. 3613-3623. Especially, p. 3613, abstract.

Simm R et al. Phenotypic convergence mediated by GGDEF-domain-containing proteins. Journal of Bacteriology. Oct. 2005, vol. 187(19), pp. 6816-6823. Especially, p. 6816, abstract.

*Primary Examiner* — Jennifer Graser
(74) *Attorney, Agent, or Firm* — Ladas & Parry

(57) ABSTRACT

Method for producing multiple modifications in the chromosome of Gram-negative bacteria and *Salmonella* strains which are deficient in c-di-GMP synthesis obtained by said method. The method can be used to make multiple modifications in the genome of Gram-negative bacteria, simply and efficiently, using the plasmids of the invention, which comprise a marker gene under the control of a constitutive promoter, a replication origin specific for Gram-negative bacteria, a gene which encodes a heat-sensitive protein essential for initiating replication of the plasmid, making the replication origin heat-sensitive, and a counter-selection gene. The invention also relates to mutant *Salmonella enterica* strains obtained using the method of the invention in which some of the twelve genes which encode proteins with GGDEF domain have been selected*, and to the use thereof as expression vectors, immunotherapeutic agents and in metabolic studies.

7 Claims, 10 Drawing Sheets

SEQUENCE LISTING

<160> NUMBER OF SEQ ID NOS: 112

<210> SEQ ID NO 1
<211> LENGTH: 26
<212> TYPE: DNA
<213> ORGANISM: Artificial Sequence
<220> FEATURE:
<223> OTHER INFORMATION: 01-A: PCR primer

<400> SEQUENCE: 1

```
gcggccgctg ccagtgtaac tgtgga                                          26

<210> SEQ ID NO 2
<211> LENGTH: 28
<212> TYPE: DNA
<213> ORGANISM: Artificial Sequence
<220> FEATURE:
<223> OTHER INFORMATION: 01-B: PCR primer

<400> SEQUENCE: 2
ctcgagacaa ttttcccaaa ttatagaa                                        28

<210> SEQ ID NO 3
<211> LENGTH: 23
<212> TYPE: DNA
<213> ORGANISM: Artificial Sequence
<220> FEATURE:
<223> OTHER INFORMATION: 01-C: PCR primer

<400> SEQUENCE: 3
ctcgaggccg ggcttcagga ttt                                             23

<210> SEQ ID NO 4
<211> LENGTH: 23
<212> TYPE: DNA
<213> ORGANISM: Artificial Sequence
<220> FEATURE:
<223> OTHER INFORMATION: 01-D: PCR primer

<400> SEQUENCE: 4
agatctctgg gacacgaccg taa                                             23

<210> SEQ ID NO 5
<211> LENGTH: 20
<212> TYPE: DNA
<213> ORGANISM: Artificial Sequence
<220> FEATURE:
<223> OTHER INFORMATION: 01-E: PCR primer

<400> SEQUENCE: 5
cacagttgtt ataacgttac                                                 20

<210> SEQ ID NO 6
<211> LENGTH: 18
<212> TYPE: DNA
<213> ORGANISM: Artificial Sequence
<220> FEATURE:
<223> OTHER INFORMATION: 01-F: PCR primer

<400> SEQUENCE: 6
cctgaacaaa gactcgct                                                   18

<210> SEQ ID NO 7
<211> LENGTH: 80
<212> TYPE: DNA
<213> ORGANISM: Artificial Sequence
<220> FEATURE:
<223> OTHER INFORMATION: yeaJ-Km Fw: PCR primer

<400> SEQUENCE: 7
tttcggcttt atcgcaacgt cacacgcgaa aatattagcg atgccatgac cgggctttac     60
aaagccacgt tgtgtctcaa                                                 80

<210> SEQ ID NO 8
<211> LENGTH: 80
```

```
<212> TYPE: DNA
<213> ORGANISM: Artificial Sequence
<220> FEATURE:
<223> OTHER INFORMATION: yeaJ-Km Rw: PCR primer

<400> SEQUENCE: 8
gggctgcata ttataaatcc cggcagaaaa atggactgtc ttatccggtg cgataatttg      60
gcgctgaggt ctgcctcgtg                                                  80

<210> SEQ ID NO 9
<211> LENGTH: 80
<212> TYPE: DNA
<213> ORGANISM: Artificial Sequence
<220> FEATURE:
<223> OTHER INFORMATION: 02 Clo-Fw: PCR primer

<400> SEQUENCE: 9
atgaatttgc atcataaagc gctcaggcac tttatctcgg caagcgtcat cgttttgaca      60
gtgtaggctg gagctgcttc                                                  80

<210> SEQ ID NO 10
<211> LENGTH: 80
<212> TYPE: DNA
<213> ORGANISM: Artificial Sequence
<220> FEATURE:
<223> OTHER INFORMATION: 02 Clo-Rv: PCR primer

<400> SEQUENCE: 10
ctatgatgaa cgatgttgtt tttgttgttt gttcagatag agctgcgcat cggaagcctg      60
catatgaata tcctccttag                                                  80

<210> SEQ ID NO 11
<211> LENGTH: 18
<212> TYPE: DNA
<213> ORGANISM: Artificial Sequence
<220> FEATURE:
<223> OTHER INFORMATION: yeaJ Fw: PCR primer

<400> SEQUENCE: 11
tgactttaca gaccagcg                                                    18

<210> SEQ ID NO 12
<211> LENGTH: 18
<212> TYPE: DNA
<213> ORGANISM: Artificial Sequence
<220> FEATURE:
<223> OTHER INFORMATION: yeaJ Rv: PCR primer

<400> SEQUENCE: 12
agcgccaatc aaagtgca                                                    18

<210> SEQ ID NO 13
<211> LENGTH: 26
<212> TYPE: DNA
<213> ORGANISM: Artificial Sequence
<220> FEATURE:
<223> OTHER INFORMATION: 03-A: PCR primer

<400> SEQUENCE: 13
gcggccgcga tatcacccaa caaatg                                           26

<210> SEQ ID NO 14
<211> LENGTH: 24
<212> TYPE: DNA
<213> ORGANISM: Artificial Sequence
```

```
-continued

<220> FEATURE:
<223> OTHER INFORMATION: 03-B: PCR primer

<400> SEQUENCE: 14
ctcgagcatc ccatttaagc gcca                                    24

<210> SEQ ID NO 15
<211> LENGTH: 25
<212> TYPE: DNA
<213> ORGANISM: Artificial Sequence
<220> FEATURE:
<223> OTHER INFORMATION: 03-C: PCR primer

<400> SEQUENCE: 15
ctcgagcgat aatagggaga acagc                                   25

<210> SEQ ID NO 16
<211> LENGTH: 25
<212> TYPE: DNA
<213> ORGANISM: Artificial Sequence
<220> FEATURE:
<223> OTHER INFORMATION: 03-D: PCR primer

<400> SEQUENCE: 16
agatctcaga tacgccggta atttt                                   25

<210> SEQ ID NO 17
<211> LENGTH: 17
<212> TYPE: DNA
<213> ORGANISM: Artificial Sequence
<220> FEATURE:
<223> OTHER INFORMATION: 03-E: PCR primer

<400> SEQUENCE: 17
tggacctctc ctatccg                                            17

<210> SEQ ID NO 18
<211> LENGTH: 19
<212> TYPE: DNA
<213> ORGANISM: Artificial Sequence
<220> FEATURE:
<223> OTHER INFORMATION: 03-F: PCR primer

<400> SEQUENCE: 18
tgctgctgcc attttcaat                                          19

<210> SEQ ID NO 19
<211> LENGTH: 26
<212> TYPE: DNA
<213> ORGANISM: Artificial Sequence
<220> FEATURE:
<223> OTHER INFORMATION: 04-A: PCR primer

<400> SEQUENCE: 19
gcggccgcgg aattgtcgta cacggt                                  26

<210> SEQ ID NO 20
<211> LENGTH: 26
<212> TYPE: DNA
<213> ORGANISM: Artificial Sequence
<220> FEATURE:
<223> OTHER INFORMATION: 04-B: PCR primer

<400> SEQUENCE: 20
ctcgagaact tctggttatt gataca                                  26
```

```
<210> SEQ ID NO 21
<211> LENGTH: 23
<212> TYPE: DNA
<213> ORGANISM: Artificial Sequence
<220> FEATURE:
<223> OTHER INFORMATION: 04-C: PCR primer

<400> SEQUENCE: 21
ctccagcctt cgcgccagcc atc                                     23

<210> SEQ ID NO 22
<211> LENGTH: 24
<212> TYPE: DNA
<213> ORGANISM: Artificial Sequence
<220> FEATURE:
<223> OTHER INFORMATION: 04-D: PCR primer

<400> SEQUENCE: 22
agatctctca caacgaaatc cgcc                                    24

<210> SEQ ID NO 23
<211> LENGTH: 16
<212> TYPE: DNA
<213> ORGANISM: Artificial Sequence
<220> FEATURE:
<223> OTHER INFORMATION: 04-E: PCR primer

<400> SEQUENCE: 23
agcgtagcgt cctggc                                             16

<210> SEQ ID NO 24
<211> LENGTH: 18
<212> TYPE: DNA
<213> ORGANISM: Artificial Sequence
<220> FEATURE:
<223> OTHER INFORMATION: 04-F: PCR primer

<400> SEQUENCE: 24
ccaactggac gttcattg                                           18

<210> SEQ ID NO 25
<211> LENGTH: 26
<212> TYPE: DNA
<213> ORGANISM: Artificial Sequence
<220> FEATURE:
<223> OTHER INFORMATION: 05-A: PCR primer

<400> SEQUENCE: 25
gcggccgcac cggtaattca atcgcc                                  26

<210> SEQ ID NO 26
<211> LENGTH: 23
<212> TYPE: DNA
<213> ORGANISM: Artificial Sequence
<220> FEATURE:
<223> OTHER INFORMATION: 05-B: PCR primer

<400> SEQUENCE: 26
ctcgagtcta tccgaatcgc cgg                                     23

<210> SEQ ID NO 27
<211> LENGTH: 23
<212> TYPE: DNA
<213> ORGANISM: Artificial Sequence
<220> FEATURE:
<223> OTHER INFORMATION: 05-C: PCR primer

<400> SEQUENCE: 27
```

```
ctcgagccag ccgtgggtat acc                                          23
```

```
<210> SEQ ID NO 28
<211> LENGTH: 23
<212> TYPE: DNA
<213> ORGANISM: Artificial Sequence
<220> FEATURE:
<223> OTHER INFORMATION: 05-D: PCR primer

<400> SEQUENCE: 28
agatctgttt gaacagggcg tgc                                          23
```

```
<210> SEQ ID NO 29
<211> LENGTH: 18
<212> TYPE: DNA
<213> ORGANISM: Artificial Sequence
<220> FEATURE:
<223> OTHER INFORMATION: 05-E: PCR primer

<400> SEQUENCE: 29
atctcttcac gcaaacgc                                                18
```

```
<210> SEQ ID NO 30
<211> LENGTH: 18
<212> TYPE: DNA
<213> ORGANISM: Artificial Sequence
<220> FEATURE:
<223> OTHER INFORMATION: 05-F: PCR primer

<400> SEQUENCE: 30
cgcgtctgtt tgatcttg                                                18
```

```
<210> SEQ ID NO 31
<211> LENGTH: 26
<212> TYPE: DNA
<213> ORGANISM: Artificial Sequence
<220> FEATURE:
<223> OTHER INFORMATION: 06-A: PCR primer

<400> SEQUENCE: 31
gcggccgccg tcatccgttc cttgaa                                       26
```

```
<210> SEQ ID NO 32
<211> LENGTH: 28
<212> TYPE: DNA
<213> ORGANISM: Artificial Sequence
<220> FEATURE:
<223> OTHER INFORMATION: 06-B: PCR primer

<400> SEQUENCE: 32
ctcgagaatg ctcacatcat tatataag                                     28
```

```
<210> SEQ ID NO 33
<211> LENGTH: 25
<212> TYPE: DNA
<213> ORGANISM: Artificial Sequence
<220> FEATURE:
<223> OTHER INFORMATION: 06-C: PCR primer

<400> SEQUENCE: 33
ctcgagtaaa aaaccgggg atagc                                         25
```

```
<210> SEQ ID NO 34
<211> LENGTH: 24
<212> TYPE: DNA
<213> ORGANISM: Artificial Sequence
```

-continued

```
<220> FEATURE:
<223> OTHER INFORMATION: 06-D: PCR primer

<400> SEQUENCE: 34
agatctaagt ggcgattatc gtcg                                              24

<210> SEQ ID NO 35
<211> LENGTH: 17
<212> TYPE: DNA
<213> ORGANISM: Artificial Sequence
<220> FEATURE:
<223> OTHER INFORMATION: 06-E: PCR primer

<400> SEQUENCE: 35
ccaggtttgg gcgatgt                                                      17

<210> SEQ ID NO 36
<211> LENGTH: 18
<212> TYPE: DNA
<213> ORGANISM: Artificial Sequence
<220> FEATURE:
<223> OTHER INFORMATION: 06-F: PCR primer

<400> SEQUENCE: 36
tatgtcgttg atgccagc                                                     18

<210> SEQ ID NO 37
<211> LENGTH: 80
<212> TYPE: DNA
<213> ORGANISM: Artificial Sequence
<220> FEATURE:
<223> OTHER INFORMATION: 06 Clo-Fw: PCR primer

<400> SEQUENCE: 37
atgccggata agtgtaacgt attaaaaaat ataaaaatat tcttactggc cttctgcctg       60
gtgtaggctg gagctgcttc                                                   80

<210> SEQ ID NO 38
<211> LENGTH: 80
<212> TYPE: DNA
<213> ORGANISM: Artificial Sequence
<220> FEATURE:
<223> OTHER INFORMATION: 06 Clo-Rv: PCR primer

<400> SEQUENCE: 38
ttatttgcct aacgggcgcg ggcggccaat cagatatccc tgcaaactgt gtacgccaag       60
catatgaata tcctccttag                                                   80

<210> SEQ ID NO 39
<211> LENGTH: 28
<212> TYPE: DNA
<213> ORGANISM: Artificial Sequence
<220> FEATURE:
<223> OTHER INFORMATION: 07-A: PCR primer

<400> SEQUENCE: 39
gcggccgcga cgatatggca aaataatg                                          28

<210> SEQ ID NO 40
<211> LENGTH: 25
<212> TYPE: DNA
<213> ORGANISM: Artificial Sequence
<220> FEATURE:
<223> OTHER INFORMATION: 07-B: PCR primer

<400> SEQUENCE: 40
```
ctcgaggatt ccgtgcaagc attaa                25

<210> SEQ ID NO 41
<211> LENGTH: 22
<212> TYPE: DNA
<213> ORGANISM: Artificial Sequence
<220> FEATURE:
<223> OTHER INFORMATION: 07-C: PCR primer

<400> SEQUENCE: 41
ctcgagggcc tggccgtttc tg                   22

<210> SEQ ID NO 42
<211> LENGTH: 25
<212> TYPE: DNA
<213> ORGANISM: Artificial Sequence
<220> FEATURE:
<223> OTHER INFORMATION: 07-D: PCR primer

<400> SEQUENCE: 42
agatctagca acttgaacaa gagca                25

<210> SEQ ID NO 43
<211> LENGTH: 20
<212> TYPE: DNA
<213> ORGANISM: Artificial Sequence
<220> FEATURE:
<223> OTHER INFORMATION: 07-E: PCR primer

<400> SEQUENCE: 43
gattattttt tctccgcaca                      20

<210> SEQ ID NO 44
<211> LENGTH: 19
<212> TYPE: DNA
<213> ORGANISM: Artificial Sequence
<220> FEATURE:
<223> OTHER INFORMATION: 07-F: PCR primer

<400> SEQUENCE: 44
cttagaagac ctgaacttc                       19

<210> SEQ ID NO 45
<211> LENGTH: 26
<212> TYPE: DNA
<213> ORGANISM: Artificial Sequence
<220> FEATURE:
<223> OTHER INFORMATION: 08-A: PCR primer

<400> SEQUENCE: 45
gcggccgcca cagcatggcg gtaaaa               26

<210> SEQ ID NO 46
<211> LENGTH: 25
<212> TYPE: DNA
<213> ORGANISM: Artificial Sequence
<220> FEATURE:
<223> OTHER INFORMATION: 08-B: PCR primer

<400> SEQUENCE: 46
ctcgaggtta actccgacgg ttata                25

<210> SEQ ID NO 47
<211> LENGTH: 27
<212> TYPE: DNA
<213> ORGANISM: Artificial Sequence

```
<220> FEATURE:
<223> OTHER INFORMATION: 08-C: PCR primer

<400> SEQUENCE: 47
ctcgaggttt aatttgtttt cacgtag                                        27

<210> SEQ ID NO 48
<211> LENGTH: 23
<212> TYPE: DNA
<213> ORGANISM: Artificial Sequence
<220> FEATURE:
<223> OTHER INFORMATION: 08-D: PCR primer

<400> SEQUENCE: 48
agatctgata ttgcccggcg tac                                            23

<210> SEQ ID NO 49
<211> LENGTH: 18
<212> TYPE: DNA
<213> ORGANISM: Artificial Sequence
<220> FEATURE:
<223> OTHER INFORMATION: 08-E: PCR primer

<400> SEQUENCE: 49
gatagcccag cttatgca                                                  18

<210> SEQ ID NO 50
<211> LENGTH: 18
<212> TYPE: DNA
<213> ORGANISM: Artificial Sequence
<220> FEATURE:
<223> OTHER INFORMATION: 08-F: PCR primer

<400> SEQUENCE: 50
cgcataaagc tgttgctg                                                  18

<210> SEQ ID NO 51
<211> LENGTH: 25
<212> TYPE: DNA
<213> ORGANISM: Artificial Sequence
<220> FEATURE:
<223> OTHER INFORMATION: 09-A: PCR primer

<400> SEQUENCE: 51
gcggccgcag tttcaccaca ggcgc                                          25

<210> SEQ ID NO 52
<211> LENGTH: 26
<212> TYPE: DNA
<213> ORGANISM: Artificial Sequence
<220> FEATURE:
<223> OTHER INFORMATION: 09-B: PCR primer

<400> SEQUENCE: 52
ctcgagttag ctcattggtt atgcag                                         26

<210> SEQ ID NO 53
<211> LENGTH: 23
<212> TYPE: DNA
<213> ORGANISM: Artificial Sequence
<220> FEATURE:
<223> OTHER INFORMATION: 09-B: PCR primer

<400> SEQUENCE: 53
ctcgaggctt cttccgcctg ttg                                            23
```

```
<210> SEQ ID NO 54
<211> LENGTH: 26
<212> TYPE: DNA
<213> ORGANISM: Artificial Sequence
<220> FEATURE:
<223> OTHER INFORMATION: 09-D: PCR primer

<400> SEQUENCE: 54
agatctttga gaataaaacg cagttg                                              26

<210> SEQ ID NO 55
<211> LENGTH: 18
<212> TYPE: DNA
<213> ORGANISM: Artificial Sequence
<220> FEATURE:
<223> OTHER INFORMATION: 09-E: PCR primer

<400> SEQUENCE: 55
cgcgtacgtt atctgatg                                                       18

<210> SEQ ID NO 56
<211> LENGTH: 18
<212> TYPE: DNA
<213> ORGANISM: Artificial Sequence
<220> FEATURE:
<223> OTHER INFORMATION: 09-F: PCR primer

<400> SEQUENCE: 56
ttgaaaccgc tattggcg                                                       18

<210> SEQ ID NO 57
<211> LENGTH: 26
<212> TYPE: DNA
<213> ORGANISM: Artificial Sequence
<220> FEATURE:
<223> OTHER INFORMATION: 10-A: PCR primer

<400> SEQUENCE: 57
gcggccgcta tagcccgcag gaatac                                              26

<210> SEQ ID NO 58
<211> LENGTH: 25
<212> TYPE: DNA
<213> ORGANISM: Artificial Sequence
<220> FEATURE:
<223> OTHER INFORMATION: 10-B: PCR primer

<400> SEQUENCE: 58
ctcgagaatt gttaacgagc ggctg                                               25

<210> SEQ ID NO 59
<211> LENGTH: 22
<212> TYPE: DNA
<213> ORGANISM: Artificial Sequence
<220> FEATURE:
<223> OTHER INFORMATION: 10-C: PCR primer

<400> SEQUENCE: 59
ctcgagtcgg cgttgtgcga gc                                                  22

<210> SEQ ID NO 60
<211> LENGTH: 23
<212> TYPE: DNA
<213> ORGANISM: Artificial Sequence
<220> FEATURE:
<223> OTHER INFORMATION: 10-D: PCR primer

<400> SEQUENCE: 60
```

```
agactcatcg agcgttgccg gat                                              23

<210> SEQ ID NO 61
<211> LENGTH: 20
<212> TYPE: DNA
<213> ORGANISM: Artificial Sequence
<220> FEATURE:
<223> OTHER INFORMATION: 10-E: PCR primer

<400> SEQUENCE: 61
aggtgattaa cgagaataac                                                  20

<210> SEQ ID NO 62
<211> LENGTH: 20
<212> TYPE: DNA
<213> ORGANISM: Artificial Sequence
<220> FEATURE:
<223> OTHER INFORMATION: 10-F: PCR primer

<400> SEQUENCE: 62
caatcacatt gaaaatgagc                                                  20

<210> SEQ ID NO 63
<211> LENGTH: 27
<212> TYPE: DNA
<213> ORGANISM: Artificial Sequence
<220> FEATURE:
<223> OTHER INFORMATION: 11-A: PCR primer

<400> SEQUENCE: 63
gcggccgcgt aagataactg tgcgaag                                          27

<210> SEQ ID NO 64
<211> LENGTH: 26
<212> TYPE: DNA
<213> ORGANISM: Artificial Sequence
<220> FEATURE:
<223> OTHER INFORMATION: 11-B: PCR primer

<400> SEQUENCE: 64
ctcgagttgt cgttatttat cggtga                                           26

<210> SEQ ID NO 65
<211> LENGTH: 24
<212> TYPE: DNA
<213> ORGANISM: Artificial Sequence
<220> FEATURE:
<223> OTHER INFORMATION: 11-C: PCR primer

<400> SEQUENCE: 65
ctcgagttgg cgtaatcgtg ctac                                             24

<210> SEQ ID NO 66
<211> LENGTH: 24
<212> TYPE: DNA
<213> ORGANISM: Artificial Sequence
<220> FEATURE:
<223> OTHER INFORMATION: 11-D: PCR primer

<400> SEQUENCE: 66
agatcttcct gatgcacatc aagc                                             24

<210> SEQ ID NO 67
<211> LENGTH: 18
<212> TYPE: DNA
<213> ORGANISM: Artificial Sequence
```

```
<220> FEATURE:
<223> OTHER INFORMATION: 11-E: PCR primer

<400> SEQUENCE: 67
aaggtggcgg aattggta                                                  18

<210> SEQ ID NO 68
<211> LENGTH: 18
<212> TYPE: DNA
<213> ORGANISM: Artificial Sequence
<220> FEATURE:
<223> OTHER INFORMATION: 11-F: PCR primer

<400> SEQUENCE: 68
ccggtattgc tccagata                                                  18

<210> SEQ ID NO 69
<211> LENGTH: 27
<212> TYPE: DNA
<213> ORGANISM: Artificial Sequence
<220> FEATURE:
<223> OTHER INFORMATION: 12-A: PCR primer

<400> SEQUENCE: 69
gcggccgcta acagcttaac gttgtcc                                        27

<210> SEQ ID NO 70
<211> LENGTH: 23
<212> TYPE: DNA
<213> ORGANISM: Artificial Sequence
<220> FEATURE:
<223> OTHER INFORMATION: 12-B: PCR primer

<400> SEQUENCE: 70
ctcgagtcag cagaaccccc caa                                            23

<210> SEQ ID NO 71
<211> LENGTH: 23
<212> TYPE: DNA
<213> ORGANISM: Artificial Sequence
<220> FEATURE:
<223> OTHER INFORMATION: 12-C: PCR primer

<400> SEQUENCE: 71
ctcgagacgc cgcggcgcgg cgt                                            23

<210> SEQ ID NO 72
<211> LENGTH: 24
<212> TYPE: DNA
<213> ORGANISM: Artificial Sequence
<220> FEATURE:
<223> OTHER INFORMATION: 12-D: PCR primer

<400> SEQUENCE: 72
agatctcagc ttgaagcgtt gctt                                           24

<210> SEQ ID NO 73
<211> LENGTH: 17
<212> TYPE: DNA
<213> ORGANISM: Artificial Sequence
<220> FEATURE:
<223> OTHER INFORMATION: 12-E: PCR primer

<400> SEQUENCE: 73
tcccgcggtt gctctt                                                    17
```

```
<210> SEQ ID NO 74
<211> LENGTH: 17
<212> TYPE: DNA
<213> ORGANISM: Artificial Sequence
<220> FEATURE:
<223> OTHER INFORMATION: 12-F: PCR primer

<400> SEQUENCE: 74
aacaggccag acgcgtg                                                    17

<210> SEQ ID NO 75
<211> LENGTH: 29
<212> TYPE: DNA
<213> ORGANISM: Artificial Sequence
<220> FEATURE:
<223> OTHER INFORMATION: 02-H: PCR primer

<400> SEQUENCE: 75
gcggccgcat gaatttgcat cataaagcg                                       29

<210> SEQ ID NO 76
<211> LENGTH: 26
<212> TYPE: DNA
<213> ORGANISM: Artificial Sequence
<220> FEATURE:
<223> OTHER INFORMATION: 02-I: PCR primer

<400> SEQUENCE: 76
agatctctat gatgaacgat gttgtt                                          26

<210> SEQ ID NO 77
<211> LENGTH: 17
<212> TYPE: DNA
<213> ORGANISM: Artificial Sequence
<220> FEATURE:
<223> OTHER INFORMATION: adrAint.Fw:  PCR primer

<400> SEQUENCE: 77
cggctattca ctgtcgg                                                    17

<210> SEQ ID NO 78
<211> LENGTH: 20
<212> TYPE: DNA
<213> ORGANISM: Artificial Sequence
<220> FEATURE:
<223> OTHER INFORMATION: adrA int.Rv:  PCR primer

<400> SEQUENCE: 78
tagcgttatc tgtaattgac                                                 20

<210> SEQ ID NO 79
<211> LENGTH: 17
<212> TYPE: DNA
<213> ORGANISM: Artificial Sequence
<220> FEATURE:
<223> OTHER INFORMATION: yeaJ int.Fw:  PCR primer

<400> SEQUENCE: 79
acaccggtgc tggaaca                                                    17

<210> SEQ ID NO 80
<211> LENGTH: 18
<212> TYPE: DNA
<213> ORGANISM: Artificial Sequence
<220> FEATURE:
<223> OTHER INFORMATION: yeaJ int.Rv:  PCR primer

<400> SEQUENCE: 80
```

```
acgaataata cgctccgg                                                 18

<210> SEQ ID NO 81
<211> LENGTH: 16
<212> TYPE: DNA
<213> ORGANISM: Artificial Sequence
<220> FEATURE:
<223> OTHER INFORMATION: yciR int.Fw:  PCR primer

<400> SEQUENCE: 81
accggcctgc ccaatc                                                   16

<210> SEQ ID NO 82
<211> LENGTH: 17
<212> TYPE: DNA
<213> ORGANISM: Artificial Sequence
<220> FEATURE:
<223> OTHER INFORMATION: yciR int.Rv:  PCR primer

<400> SEQUENCE: 82
gccgcgccag gtaattt                                                  17

<210> SEQ ID NO 83
<211> LENGTH: 17
<212> TYPE: DNA
<213> ORGANISM: Artificial Sequence
<220> FEATURE:
<223> OTHER INFORMATION: DGC II.Fw:  PCR primer

<400> SEQUENCE: 83
gatgaccaaa gcgatcg                                                  17

<210> SEQ ID NO 84
<211> LENGTH: 17
<212> TYPE: DNA
<213> ORGANISM: Artificial Sequence
<220> FEATURE:
<223> OTHER INFORMATION: DGC III.Rv:  PCR primer

<400> SEQUENCE: 84
agtgacagcc agtctac                                                  17

<210> SEQ ID NO 85
<211> LENGTH: 18
<212> TYPE: DNA
<213> ORGANISM: Artificial Sequence
<220> FEATURE:
<223> OTHER INFORMATION: yegE VI.Fw:  PCR primer

<400> SEQUENCE: 85
tgactctatc ggagaagc                                                 18

<210> SEQ ID NO 86
<211> LENGTH: 18
<212> TYPE: DNA
<213> ORGANISM: Artificial Sequence
<220> FEATURE:
<223> OTHER INFORMATION: yegE V.Rv:  PCR primer

<400> SEQUENCE: 86
aacaggccaa actcatcg                                                 18

<210> SEQ ID NO 87
<211> LENGTH: 15
<212> TYPE: DNA
<213> ORGANISM: Artificial Sequence
```

```
<220> FEATURE:
<223> OTHER INFORMATION: yfeA probe Fw:  PCR primer

<400> SEQUENCE: 87
gcgctggcgc tacgg                                                         15

<210> SEQ ID NO 88
<211> LENGTH: 18
<212> TYPE: DNA
<213> ORGANISM: Artificial Sequence
<220> FEATURE:
<223> OTHER INFORMATION: yfeA probe Rv:  PCR primer

<400> SEQUENCE: 88
cggttatagc taagcagg                                                      18

<210> SEQ ID NO 89
<211> LENGTH: 18
<212> TYPE: DNA
<213> ORGANISM: Artificial Sequence
<220> FEATURE:
<223> OTHER INFORMATION: yfiN III.Fw:  PCR primer

<400> SEQUENCE: 89
ttccattgcc ggtatcac                                                      18

<210> SEQ ID NO 90
<211> LENGTH: 18
<212> TYPE: DNA
<213> ORGANISM: Artificial Sequence
<220> FEATURE:
<223> OTHER INFORMATION: yfiN III.Rv:  PCR primer

<400> SEQUENCE: 90
atacagctgc gaaatgcc                                                      18

<210> SEQ ID NO 91
<211> LENGTH: 17
<212> TYPE: DNA
<213> ORGANISM: Artificial Sequence
<220> FEATURE:
<223> OTHER INFORMATION: yhdA int.Rv:  PCR primer

<400> SEQUENCE: 91
gttagccggt agcgcat                                                       17

<210> SEQ ID NO 92
<211> LENGTH: 17
<212> TYPE: DNA
<213> ORGANISM: Artificial Sequence
<220> FEATURE:
<223> OTHER INFORMATION: yhdA int.Rv:  PCR primer

<400> SEQUENCE: 92
tttatcggtg cgctggc                                                       17

<210> SEQ ID NO 93
<211> LENGTH: 19
<212> TYPE: DNA
<213> ORGANISM: Artificial Sequence
<220> FEATURE:
<223> OTHER INFORMATION: stm3388 IV.Fw;  PCR primer

<400> SEQUENCE: 93
tatcagcgtt atatgccct                                                     19
```

```
<210> SEQ ID NO 94
<211> LENGTH: 17
<212> TYPE: DNA
<213> ORGANISM: Artificial Sequence
<220> FEATURE:
<223> OTHER INFORMATION: stm3388 V.Rv:  PCR primer

<400> SEQUENCE: 94
atagctcacg ccgacag                                                  17

<210> SEQ ID NO 95
<211> LENGTH: 19
<212> TYPE: DNA
<213> ORGANISM: Artificial Sequence
<220> FEATURE:
<223> OTHER INFORMATION: yhjK int.Fv:  PCR primer

<400> SEQUENCE: 95
ttaatgaacg actgcccat                                                19

<210> SEQ ID NO 96
<211> LENGTH: 16
<212> TYPE: DNA
<213> ORGANISM: Artificial Sequence
<220> FEATURE:
<223> OTHER INFORMATION: yhjK int.Rv:  PCR primer

<400> SEQUENCE: 96
cggcagcgtg tggatc                                                   16

<210> SEQ ID NO 97
<211> LENGTH: 18
<212> TYPE: DNA
<213> ORGANISM: Artificial Sequence
<220> FEATURE:
<223> OTHER INFORMATION: stm4551 III.Fw:  PCR primer

<400> SEQUENCE: 97
gcccatcata tgaccgta                                                 18

<210> SEQ ID NO 98
<211> LENGTH: 18
<212> TYPE: DNA
<213> ORGANISM: Artificial Sequence
<220> FEATURE:
<223> OTHER INFORMATION: stm4551 II.Rv:  PCR primer

<400> SEQUENCE: 98
ctctcgtttt cccccttt                                                 18

<210> SEQ ID NO 99
<211> LENGTH: 19
<212> TYPE: DNA
<213> ORGANISM: Artificial Sequence
<220> FEATURE:
<223> OTHER INFORMATION: stm2503 int.Fw:  PCR primer

<400> SEQUENCE: 99
tatcagcgtt atatgccct                                                19

<210> SEQ ID NO 100
<211> LENGTH: 17
<212> TYPE: DNA
<213> ORGANISM: Artificial Sequence
<220> FEATURE:
<223> OTHER INFORMATION: stm2503 int.Rv:  PCR primer

<400> SEQUENCE: 100
```

```
atagctcacg ccgacag                                                    17

<210> SEQ ID NO 101
<211> LENGTH: 18
<212> TYPE: DNA
<213> ORGANISM: Artificial Sequence
<220> FEATURE:
<223> OTHER INFORMATION: 02-E:  PCR primer

<400> SEQUENCE: 101
agcatattcg cgatcagg                                                   18

<210> SEQ ID NO 102
<211> LENGTH: 27
<212> TYPE: DNA
<213> ORGANISM: Artificial Sequence
<220> FEATURE:
<223> OTHER INFORMATION: 02-J:  PCR primer

<400> SEQUENCE: 102
ctcgagcgct ttatgatgca aattcat                                         27

<210> SEQ ID NO 103
<211> LENGTH: 26
<212> TYPE: DNA
<213> ORGANISM: Artificial Sequence
<220> FEATURE:
<223> OTHER INFORMATION: 02-C:  PCR primer

<400> SEQUENCE: 103
ctcgaggcag taaatgttca tattgc                                          26

<210> SEQ ID NO 104
<211> LENGTH: 23
<212> TYPE: DNA
<213> ORGANISM: Artificial Sequence
<220> FEATURE:
<223> OTHER INFORMATION: 02-D:  PCR primer

<400> SEQUENCE: 104
agatctggcg atgcgcagat agt                                             23

<210> SEQ ID NO 105
<211> LENGTH: 20
<212> TYPE: DNA
<213> ORGANISM: Artificial Sequence
<220> FEATURE:
<223> OTHER INFORMATION: rpoS_1_Fw:  PCR primer

<400> SEQUENCE: 105
gaattgtata caatcgccag                                                 20

<210> SEQ ID NO 106
<211> LENGTH: 23
<212> TYPE: DNA
<213> ORGANISM: Artificial Sequence
<220> FEATURE:
<223> OTHER INFORMATION: rpoS-B:  PCR primer

<400> SEQUENCE: 106
ctcgaggctc ctacccgtga tcc                                             23

<210> SEQ ID NO 107
<211> LENGTH: 26
<212> TYPE: DNA
<213> ORGANISM: Artificial Sequence
```

```
<220> FEATURE:
<223> OTHER INFORMATION: rpoS-C:  PCR primer

<400> SEQUENCE: 107
ctcgagttgt caaaaaaagg ccagtc                                          26

<210> SEQ ID NO 108
<211> LENGTH: 24
<212> TYPE: DNA
<213> ORGANISM: Artificial Sequence
<220> FEATURE:
<223> OTHER INFORMATION: rpoS-D:  PCR primer

<400> SEQUENCE: 108
agatctaatc tgccacaggt gatg                                            24

<210> SEQ ID NO 109
<211> LENGTH: 18
<212> TYPE: DNA
<213> ORGANISM: Artificial Sequence
<220> FEATURE:
<223> OTHER INFORMATION: 02-K:  PCR primer

<400> SEQUENCE: 109
tatgaacatc tgcaggcg                                                   18

<210> SEQ ID NO 110
<211> LENGTH: 18
<212> TYPE: DNA
<213> ORGANISM: Artificial Sequence
<220> FEATURE:
<223> OTHER INFORMATION: 02-F:  PCR primer

<400> SEQUENCE: 110
cgttgtgtcg gtattgct                                                   18

<210> SEQ ID NO 111
<211> LENGTH: 18
<212> TYPE: DNA
<213> ORGANISM: Artificial Sequence
<220> FEATURE:
<223> OTHER INFORMATION: rpoS-E:  PCR primer

<400> SEQUENCE: 111
cgcaaattca acccgttc                                                   18

<210> SEQ ID NO 112
<211> LENGTH: 18
<212> TYPE: DNA
<213> ORGANISM: Artificial Sequence
<220> FEATURE:
<223> OTHER INFORMATION: rpoS-F:  PCR primer

<400> SEQUENCE: 112
agatggtgat catggtcg                                                   18
```

METHOD FOR PRODUCING MULTIPLE MODIFICATIONS IN THE CHROMOSOME OF GRAM-NEGATIVE BACTERIA AND SALMONELLA STRAINS WHICH ARE DEFICIENT IN C-DI-GMP SYNTHESIS OBTAINED BY SAID METHOD

This application is a continuation-in-part of International Application No. PCT7ES2008/070211, filed on Nov. 20, 2008, which International Application was published by the International Bureau on May 28, 2009, in Spanish language. This application also claims priority under 35 U.S.C. and/or 365 to ES200703068 filed in Spain on Nov. 21, 2007. The entire content of both of the above-mentioned PCT and Spanish applications are hereby incorporated by reference.

The present invention relates to a method of making modifications in the genome of a Gram-negative bacterium with which it is possible to perform successive multiple modifications on one and the same bacterial strain simply and effectively, as well as to the plasmids that make it possible to carry out said method. The invention also relates to two mutant strains of *Salmonella enterica* obtained by the method of the invention in which the twelve genes that encode proteins with the GGDEF domain have been deleted (mutant ΔXII::Km and mutant ΔXII::Clo) and to strains derived therefrom, or from the intermediate strains used for obtaining them, which are capable of expressing a single functional GGDEF protein, as well as to the possible uses of the aforementioned mutant *Salmonella* strains.

PRIOR ART

The GGDEF Proteins and c-di-GMP

The first link between c-di-GMP and the GGDEF proteins was made during investigation of cellulose synthesis in *Gluconacetobacter xylinus* (previously called *Acetobacter xylinum*). A pioneering article published by Moshed Benziman's group (Christensen, 1987) demonstrated that the activity of the regulatory subunit of cellulose synthetase was activated after binding the cyclic dinucleotide cyclic di-guanidine-monophosphate, c-di-GMP (FIG. 1). This work went unnoticed until, 11 years later, this same group supplied the first connection between the synthesis/degradation of c-di-GMP and the proteins with GGDEF domains (domain associated with diguanylate cyclase activity, i.e. with c-di-GMP synthesis) and/or EAL (domain associated with phosphodiesterase activity, i.e. with the degradation of c-di-GMP and which can be isolated from a polypeptide or combined with the GGDEF domain on the same protein). By reverse genetics and using the amino acid sequence of the purified proteins with diguanylate cyclase and phosphodiesterase activity, Tal et al. (Tal et al., 1998) cloned and characterized three operons implicated in the control of the levels of c-di-GMP in *G. xylinus*. Each of these operons included two genes, one gene that encoded a protein with diguanylate cyclase activity, responsible for c-di-GMP synthesis from two molecules of GTP and one gene that encoded a phosphodiesterase, responsible for the degradation of c-di-GMP to GMP. Analysis of the sequences of these enzymes revealed that the six paralogous proteins encoded by these three operons had in common the presence of two domains, which were designated GGDEF (previously DUF1, Domain of Unknown Function 1) and EAL (previously DUF2), due to the highly conserved presence of these amino acid sequences in each of them. On the basis of these results, M. Benziman's group proposed a model of regulation of cellulose synthesis in which proteins with the GGDEF domain would be responsible for c-di-GMP synthesis whereas the proteins with the EAL domain would be responsible for the degradation of c-di-GMP. The c-di-GMP would bind to the catalytic subunit of cellulose synthetase, activating cellulose synthesis allosterically.

The recent sequencing of bacterial genomes has shown that the GGDEF domain is extremely abundant, and up to 4200 proteins with the GGDEF domain have been entered in the databases. Despite their abundance, the presence of proteins with the GGDEF domain is restricted to the bacteria and no protein with this domain has been found in Archaea or Eukaryotes (Galperin, 2004). Within the bacteria, GGDEF proteins exist in the majority of the genomes sequenced, from *Aquifex* and *Thermotoga* to the α and γ Proteobacteria. The GGDEF domain is absent from the genomes of Bacteroidetes, Chlamydiales and Fusobacteria. The abundance of proteins containing this domain is very variable between the different bacterial species. Thus, the genome of *Escherichia coli* contain 19 proteins with the GGDEF domain, the genome of *Pseudomonas aeruginosa* contains 39 proteins with the GGDEF domain, *Bacillus subtilis* has 4, and the small genome of *Rickettsia prowazekii* contains a single GGDEF protein. The bacterium with the largest number of GGDEF proteins is *Vibrio vulnificus*, whose genome contains 66 proteins with the GGDEF domain.

One of the most striking aspects of the GGDEF proteins is that, despite their abundance, the vast majority of these proteins have not been linked to any biological function. Thus, until very recently, none of the 19 proteins with the GGDEF domain of *E. coli* had been linked to a biological function. The situation is similar with the 39 proteins of the genome of *Pseudomonas aeruginosa* or with the 41 proteins of the genome of *Vibrio cholerae*. After this lethargy, in the last three years and coinciding with the exhaustive investigation of the process of formation of biofilms, numerous proteins with the GGDEF domain have been described, implicated in various bacterial processes, including the synthesis of exopolysaccharides and formation of biofilm, processes of differentiation in *Caulobacter crescentus*, virulence of animal and plant pathogens and regulation of genes involved in photosynthesis in *Synechococcus elongatus* (for a review see (Romling et al., 2005, Ryan et al., 2006, Jenal & Malone, 2006, Tamayo et al., 2007)). Generally, it has been observed that high levels of c-di-GMP are associated with greater capacity of the bacterium to adhere to a substrate (sessile character), formation of biofilm and the expression of adhesive components of the extracellular matrix, whereas low levels of c-di-GMP have been linked to greater motility and virulence.

Generally, and based on the fact that the GGDEF domain is often accompanied by other sensor domains (PAS, PAC, MASE2, HAMP), it has been suggested that the GGDEF proteins might be members of a signal transduction network that would make it possible to adapt the response to external stimuli by production of the secondary signal transmitter, c-di-GMP. The question that immediately arises is how different stimuli can give rise to particular responses, if they all converge in the production of one and the same diffusible molecule, c-di-GMP, for transmitting the signal.

The abundance of proteins involved in c-di-GMP synthesis in the bacterial genomes, and the fact that their presence is exclusively restricted to the Bacteria domain, and that the presence of GGDEF proteins has not been described in any eukaryotic genome, nor in any genome of Archaea sequenced to date, make this signal messenger and its signalling pathway an interesting target for the development of substances that block its synthesis and, in consequence, the capacity to form biofilms, to adhere to surfaces, or the virulence of the bacteria.

The infections caused by bacteria of the genus *Salmonella*, both in animals and in human beings, have been the cause of great concern for many years. The development of attenuated strains of *Salmonella*, to be used for generating protection against diseases caused by the bacteria of this genus, has aroused considerable interest among researchers, who have tried to discover the pathogenicity factors of these bacteria in an attempt to combat them. Among other things, biofilm formation is an important pathogenicity factor of *Salmonella*, since this enables it to survive in environments outside of the host, including soil and water, and thus pass easily from the digestive system of the host to the environment and vice versa. The ability to form biofilms appears to be widespread among the serotypes of *Salmonella enterica* (one of the main species that gives rise to intestinal infections) and, in particular, among the serotypes *Enteritidis* (referred to hereinafter as *S. enteritidis*) and *Typhimurium* (referred to hereinafter as *S. typhimurium*).

Owing to their influence on pathogenicity and virulence, the factors that influence the biofilm-forming capacity of the species of *Salmonella* and other pathogenic species such as *Escherichia coli* have attracted considerable interest. Thus, for example, US patent application US2004/017517 claims a method for reducing the formation of biofilms in strains with capacity for this belonging to the species *E. coli* or to the genera *Salmonella, Klebsiella* or to those of related gamma-proteobacteria, by increasing the levels of the protein CsrA (abbreviation of carbon storage system), a protein that inhibits the synthesis of glycogen, proposing various alternatives: the use of an oligonucleotide that modulates its expression; increasing the expression and/or translation of genes involved in regulation of the synthesis of said protein CsrA, such as CsrB, BarA, SdiA and UvrY; increasing the activity of the protein UvrY by controlling its degree of phosphorylation or increasing the average lifetime of said protein or of its messenger RNA. The proteins of the GGDEF family, for their part, have also been the object of interest for elucidating their role in the formation of biofilms.

Analysis of the genomes of different serotypes of *Salmonella enterica* shows the presence of up to 12 proteins with the GGDEF domain (FIG. 2A). Such redundancy of paralogous proteins in this and other bacteria represents a challenge for functional studies that aim to elucidate the physiological role of the signalling pathways that have c-di-GMP as second messenger. Two proteins in this family (AdrA and the product of the gene initially identified as STM1987, shown in FIG. 2A as GcpA) have been implicated in processes of synthesis of exopolysaccharides (cellulose) and formation of biofilm (Romling et al., 2000, Garcia et al., 2004). In the case of STM1987, during an investigation for establishing why the SL1344 strain of *S. typhimurium* is unable to form biofilms both in rich growth media (LB) and in media deficient in nutrients, it was found that the gene stm1987 (which encodes a protein with a GGDEF domain, GcpA) is essential for biofilm formation in a nutrient-deficient medium (Garcia et al., 2004). In this same work, mutant strains were constructed in each of the genes that encodes a protein in which the GG[DE]EF motif was conserved (where [DE] indicates the presence of glutamic acid or of aspartic acid in this position). The genome of *Salmonella* contains six proteins (STM4551, STM2123, STM1283, STM1703, STM3388, STM2672), in addition to AdrA and STM1987 in which this domain is conserved. Analysis of the phenotype of these mutants indicated that none of them affected the production of cellulose or the formation of biofilm. However, complementation of the mutants in adrA or stm1987 with each of the other GGDEF proteins showed that the majority of the GGDEF proteins were able to compensate for the deficiency of adrA or stm1987 and therefore these proteins are functional and are functionally related, controlling the levels of c-di-GMP. These studies showed that c-di-GMP regulates, among other processes, the production of cellulose and the formation of biofilms. However, none of the studies undertaken gave rise to mutant strains that lacked more than two functional members of the GGDEF family of proteins.

The redundant presence of GGDEF proteins in the genome of the bacteria greatly complicates elucidation of the particular function of each GGDEF protein because it is not possible to rule out that the other members of the family have some influence on the phenotype under investigation when there is inactivation of just one of the proteins of this family or a reduced number of them. As noted in the research of Ute Römling's group (Simm et al., 2004, Kader et al., 2006), in which it is concluded that increased levels of c-di-GMP not only affect the biosynthesis of cellulose, but that the increase in said levels caused by the overexpression of the protein AdrA leads to activation of the biosynthesis of curli fimbriae, another component of the extracellular matrix that is produced simultaneously with cellulose, owing to which the production of both elements is regulated positively by CsgD. In these works it is also observed that raised concentrations of c-di-GMP make it possible to overcome the negative regulation exerted by the temperature on the multicellular morphotype rdar (red, dry and rough), a multicellular behaviour described in *S. enterica* and *Escherichia coli* that reflects the expression of cellulose and fimbriae of the curli type in the extracellular matrix. This negative regulation is overcome, owing to which the raised levels of c-di-GMP mean that the expression of CsgD is induced at 37° C. As in the previous case, the investigations by this group were mainly carried out with mutants in which at most a single GGDEF protein had been inactivated and in no case with strains in which more than three GGDEF proteins had been inactivated, so that their conclusions on the impact of the GGDEF proteins on cellular physiology reduced to confirming the role of CsgD as a significant regulator of the appearance of the morphotype rdar and to noting that the effect of each GGDEF protein concretely on the metabolism of the bacteria might be determined partially by the level of expression of each protein in particular.

It would be interesting to find a system that makes it possible to investigate the precise function of each of the members of the GGDEF family without the presence of other members of the same family disturbing the phenotype under investigation, preferably, the formation of biofilms and their influence on pathogenicity. The conception and, above all, the development of suitable tools for this purpose has until now been held back by the methods usually employed for modifying the bacterial genome.

Modifications of the Bacterial Genome in the Absence of Selection Markers

At present, modification of the genome of bacteria is carried out by a process in which the region of the genome that we wish to modify is cloned in a plasmid, it is submitted to the desired modification and is re-inserted in the chromosome of the bacterium by a process of homologous recombination. To facilitate selection of the bacteria in which the modification has been produced, a selection marker gene is introduced simultaneously with the modification. As used in the present specification, selection marker gene means a gene whose expression gives rise to a protein that permits the survival of the bacteria that possess it in defined growth conditions, which would give rise to blocking of their replication or to the destruction of their cellular structure in the absence of the product of said selection marker gene. A typical example of selection marker gene is the genes that confer resistance to antibiotics: in the presence of the antibiotic, the bacteria that lack the resistance gene cannot survive; in contrast, the bacteria that possess the gene whose product confers resistance to said antibiotic are capable of surviving and multiplying in the presence of the antibiotic, which in theory makes it possible to select the bacteria that possess the gene for resistance to the antibiotic and eliminate the bacteria that do not possess it. Among the genes for resistance to antibiotics, those most commonly used in methods for modification of bacterial genomes are the ones that confer resistance to ampicillin, kanamycin, tetracycline or chloramphenicol (such as the gene cat, which encodes a chloramphenicol transacetylase), genes for resistance to antibiotics or other selection marker genes, each modification requires the insertion of a gene for resistance to an antibiotic or other selection marker gene in the chromosome of the bacterium. This method has serious limitations because the number of selection markers available is small, and therefore the number of modifications that can be performed on one and the same bacterium is limited.

Moreover, if we wish to perform several modifications on the same bacterium, it is necessary to introduce a selection marker gene with each modification, generating strains that are multiresistant to antibiotics, with the important environmental drawbacks that this involves for their possible unconfined use.

To solve this problem, various methods have been developed for removing the selection markers by using site-specific recombinases: recombinase Cre-lox of the phage/plasmid P1 (Ayres et al., 1993), ParA-res (Kristensen et al., 1995), TnpR-res (Camilli et al., 1994) or the system Flp-FRT of *Saccharomyces cerevisiae* (Cherepanov & Wackernagel, 1995). The recombinases recognize specific DNA sequences that are located on either side of the selection marker, so that, after the recombination process, the marker located between the sequences is eliminated together with one of the recognition sequences. However, during the reaction in which the recombinase removes the selection marker, one of the flanking recognition sequences is not removed and remains as a "fingerprint" in the genome. After several rounds of modification in one and the same strain, the genome will have, scattered over various points thereof, recognition sequences of the recombinase. In this situation, the risk of the recombinase removing fragments of the genome contained between two recognition sequences instead of the selection marker increases significantly. Another limitation of this methodology is that it proves very difficult to carry out small modifications or substitutions within a gene, because the selection marker that accompanies the modification or the recognition sequence of the recombinase mean in their turn a large change in the DNA sequence of the bacterium that is being modified.

Another strategy used for manipulating DNA, in the absence of selection marker genes, was based on the use of counterselection systems. Here, the plasmid in which the DNA fragment that bears the modification that is desired has been cloned, is inserted into the genome of the bacterium, and in addition contains a gene that encodes an enzyme whose presence proves toxic in the presence of a particular substrate in the culture medium: this gene is called the counterselection gene. So that, once the plasmid has been integrated by a recombination process, the bacterium grows in the presence of the counterselection substrate and, in theory, only the bacteria that lose the plasmid owing to a second recombination event are capable of surviving. Various counterselection systems have been used: inhibition of growth in the presence of sucrose mediated by the sacB gene (Ried & Collmer, 1987), inhibition of growth in the presence of fusaric acid mediated by tetracycline resistance genes (Maloy & Nunn, 1981), inhibition of growth in the presence of analogues of nucleotides mediated by phosphoribosyl transferases (PRT) (Bitan-Banin et al., 2003, Fabret et al., 2002, Peck et al., 2000).

Optimization of the selection of bacteria in which a two-stage modification of the genome has been carried out, i.e. a first integration of the vector that contains the sequence with the desired modification and the loss of the vector concomitant with the deletion of the gene of interest, has been attempted with vectors in which an indicator gene is expressed. As used in the present specification, indicator gene means a gene that encodes a protein whose presence gives rise to a visible, easily identifiable characteristic, when said protein is present, indicating that the gene that encodes it is also present. In contrast to the selection or counterselection genes, the presence or absence of said protein is not determining for the survival of the host organism containing it in the selection media usually employed for its growth. The commonest indicator genes are those that encode a protein that is capable of converting a compound into a second compound of a different, easily identifiable colour. One of the genes most used for this purpose is the gene lacZ, which encodes an enzyme β-galactosidase that is able to transform the compound X-Gal (5-bromo-4-chloro-3-indolyl-beta-D-galactopyranoside) giving rise to a blue-coloured compound; thus, in the presence of the indicator gene, the organisms that possess it (bacteria transformed with the plasmid of the invention in our case) will appear blue in colour when they are incubated in the presence of X-Gal, whereas the organisms that do not possess said gene (bacteria that have not been transformed by the plasmid) will appear white in colour even though they are incubated in the presence of X-Gal.

Of the indicator genes, the one used most has been the lacZ gene from *Escherichia coli*, being inserted in a plasmid under the control of a constitutive promoter, as occurs with the vector pORI (Leenhouts et al., 1996). With said vector, however, although the presence or absence of the lacZ gene permits simple screening of the recombination events by the development of blue or white colour in the colonies in the presence of X-Gal, these plasmids lack the repA gene that encodes the protein for initiation of replication and are unable to replicate in the bacteria unless the protein RepA is supplied in trans, which requires high frequencies of transformation to obtain integrations, the use of said vectors being limited to bacteria with high efficiency of transformation.

Another strategy used for promoting integration of the plasmid and its loss after it is cut out of the chromosome is the combination of selection markers, counterselection systems and temperature-sensitive replication origins, as occurs in the vector pKO3 (Link et al., 1997), which contains a chloramphenicol resistance gene, a sacB counterselection gene and a heat-sensitive replication origin. In these systems, growth of the bacteria at a temperature greater than that above which the replication origin of the plasmid does not function as such, permits the selection of bacteria in which the plasmid has been integrated in the chromosome; later, after growing the bacteria again at the temperature permitting replication of the plasmid, the colonies resistant to sucrose and sensitive to chloramphenicol will be those that may be susceptible to splitting of the plasmid, the gene of interest having been replaced by the sequences altered previously, which we wish to insert. Practical experience has shown that this system gives rise to a large number of false positives and is not valid for carrying out routine transformations that involve several consecutive modifications in the genome of one and the same bacterium.

Accordingly, the introduction of consecutive modifications in the genomes of bacteria, and especially of Gram-negative bacteria, by a simple method and that does not give rise in the genome to alterations additional to those that we wish to introduce, has represented a bottleneck for the multiple genetic modification of the bacterial chromosome. This same problem also made it difficult to develop tools that can be used for investigating biological processes involving families of proteins which, as in the case of the GGDEF family of proteins, appear to be related in their function. The present invention provides a solution to these problems.

DESCRIPTION OF THE INVENTION

The present invention provides a simple method for modification of the chromosomal DNA of Gram-negative bacteria without the need to incorporate, additionally to the modified sequence that we wish to insert into the genome or that we wish to remove from it, a selection marker or a recognition sequence of a recombinase. This alternative method is based on combination of the systems for counterselection and for presence of an indicator gene such as lacZ.

The system is based on the use of a plasmid whose structure allows a combination of both selection systems. Thus, one object of the present invention is a plasmid that contains an indicator gene under the control of a constitutive promoter, a replication origin specific for Gram-negative bacteria, a gene that encodes a heat-sensitive protein that is essential for initiating replication of the plasmid, making the replication origin heat-sensitive (ori-ts) and a counterselection gene. It is preferable for the indicator gene to be a lacZ gene, the constitutive promoter to be the promoter of the clpB gene (pclpB) and the counterselection gene to be the sacB gene. In any case, the additional presence of a selection gene provides greater reliability in selection of the bacteria that have been transformed with the plasmid, therefore preferred embodiments of the plasmids of the invention are those that further incorporate a selection marker gene, for which it is especially preferable for the selection gene to be a gene that confers resistance to an antibiotic, for example the cat gene for resistance to chloramphenicol. The plasmid pKO3blue, which is used later in the examples of the present specification, meets all the preferences expressed and is an especially preferred embodiment of the plasmids of the invention.

To be able to amplify the plasmid and obtain copies thereof, it is necessary to transform, with said plasmid, any bacterium in which the plasmid is replicable. Therefore another object of the invention is a bacterial strain transformed with a plasmid of the invention and, in particular, the *Escherichia coli* strain XL1Blue pKO3Blue, transformed with the plasmid pKO3blue and which was used for amplifying the copies of the plasmid used in the Examples that are presented later on in the present specification.

The new plasmid (pKO3blue) was constructed on the basis of the plasmid pKO3, in which a lacZ gene was cloned from *Bacillus stearothermophilus* that encodes the β-galactosidase derived from the plasmid pMAD (Arnaud et al., 2004) (FIG. 3). The lacZ gene is expressed constitutively, being under the control of the pclpB promoter (promoter of the clpB gene of *Escherichia coli*, which codes for a chaperone essential for recovery from the damage caused by elevated temperatures) (Parsell et al., 1994) and is used for selecting insertion/excision of the plasmid during a process of homologous recombination that makes it possible to insert the desired modification into the genome, after cloning, into said plasmid, the DNA fragment that contains the modification (deletion, substitution, insertion) that we wish to transfer to the chromosome of the bacterium.

This plasmid greatly facilitates modification of the chromosome of bacteria and the selection of bacteria in which the desired modification has been introduced, since it combines the sacB-sucrose counterselection system present in the plasmid pKO3 and the presence of a heat-sensitive replication origin (concretely, the replication origin derived from the plasmid pSC101 (Link et al., 1997), which acts as replication origin in the temperature range 25-35° C., but is not functional starting from 43° C., behaviour that shows when the repA gene is present and is expressed, said gene encoding a heat-sensitive protein essential for the initiation of replication of the plasmid) together with the β-galactosidase activity introduced in said plasmid. This combination makes it far easier to distinguish between those bacteria in which the recombination process takes place with loss of the plasmid and those bacteria in which this process has not occurred.

FIG. 4 shows how the successive selection processes take place. Firstly, after transformation of the bacteria with the plasmid, those bacteria showing activity of the indicator gene are selected: the colonies that are coloured blue in the case of colonies growing on plates with a culture medium that contains X-Gal when the indicator gene is lacZ. Once selected, the transformed bacteria are incubated at the restrictive temperature (43° C. in the case of pKO3blue) in the presence of the antibiotic for which the plasmid has a resistance gene. Since the replication origin of the plasmid is not functional at said temperature, the plasmid will only be conserved in those bacteria in which the plasmid is integrated into the genome of the bacterium by a recombination process. To perform selection of bacteria in which the plasmid is integrated from those bacteria in which the plasmid is not integrated, an aliquot of the culture is plated on a plate that contains the substrate of the indicator gene (X-Gal in the case of lacZ) and several colonies in which the plasmid is possibly integrated are selected (in the case of lacZ, the colonies that have incorporated the plasmid into the genome will have a blue colour owing to expression of the β-galactosidase gene, lacZ). Starting from the colonies selected in the preceding step, the process is begun for selecting those bacteria in which excision of the plasmid took place by a second recombination event, incubating the colonies at a permissive temperature (28° C. in the case of bacteria that have integrated the recombinant pKO3blue). In this stage, as a consequence of a second recombination process, in a percentage of the population there will be excision of the plasmid, losing the β-galactosidase activity and, simultaneously, the counterselection gene and the gene that confers resistance to the antibiotic. On seeding dilutions of the culture on plates that contain the compound that permits detection of the absence or presence of the indicator gene (X-gal for lacZ) and in the presence of the counterselection compound (sucrose for the sacB gene), theoretically only those bacteria that have lost the plasmid are selected. In the case of procedures conducted with pKO3blue (which has lacZ as indicator gene and the sacB gene as counterselection gene), the bacteria will be incubated in the presence of X-gal and sucrose and the surviving bacteria should appear white in colour. It is important to note that this stage represents one of the limiting steps in the process of double recombination that takes place during allelic interchange and is a stage that gives rise to a large number of false positives in the methods prior to the technology described in this invention, a disadvantage that is avoided by the method of modification of the genome of Gram-negative bacteria of the invention, which uses the plasmids of the invention previously described. It can then be confirmed that the desired modification has been introduced into the chromosome of the selected strain, which can be done, for example, by carrying out a PCR using a pair of primers that permit amplification of the sequence that supposedly should contain the modified fragment (oligonucleotides E and F in FIG. 5).

Accordingly, another object of the invention is a method for modification of the genome of a Gram-negative bacterium that comprises the stages of:

a) cloning, into a plasmid of the invention, two DNA sequences flanking the region of the bacterial genome that is to be modified, in such a way that both sequences are contiguous in the 5'-3' direction or are separated by the DNA fragment that is to be substituted or inserted into the bacterial genome;

b) transforming the plasmid obtained in stage a) in the bacterium whose genome is to be modified;

c) selecting the strain transformed in stage b) using a culture medium that comprises the compound that gives rise to a reaction that is indicative that the bacterium in which said reaction takes place has been transformed with the plasmid from stage a) and at a temperature that permits replication of the plasmid and growth of the transformed bacteria;

d) selecting the strain that has, inserted in its genome, the plasmid with which it had been transformed by incubating it at a restrictive temperature at which the plasmid is not capable of multiplying owing to its heat-sensitive mechanism of replication;

e) incubating strains obtained in stage d) in a medium that contains the substrate that proves toxic when acted upon by the counterselection enzyme encoded by the plasmid and the compound that gives rise to a reaction that is indicative of the absence of the plasmid within the bacterium, for selecting those strains in which excision and loss of the plasmid have occurred.

In this method it is not necessary to use selection markers and therefore the number of modifications that can be performed on the same strain is unlimited. That is why a preferred embodiment of the method of the invention is a method in which stages a) to e) are repeated successively more than once, introducing a different modification in the genome in each round.

The method does not require the incorporation of any exogenous DNA sequence, so that minimal modifications of the genome can be constructed that involve the alteration of a particular nucleotide within the genome of the bacterium. Equally, the modifications can be of a greater extent and consist of:

Deletion of a DNA fragment. In this case, the two sequences flanking the region of the bacterial genome that is to be deleted will be contiguous in the plasmid of the invention with which the bacterium is transformed.

Insertion of a DNA fragment in a concrete location of the chromosome. In this case, the flanking sequences that were cloned in a plasmid in stage a) of the method of the invention, will be the adjacent sequences, to the right and left of the concrete location of the bacterial genome in which the DNA fragment is to be inserted, the sequences being cloned in such a way that said flanking sequences will be separated in the plasmid by the DNA fragment that is to be inserted.

Interchange of sequences (substitution of a fragment of the bacterial genome with a different DNA fragment in a concrete location of the chromosome. In this case, the flanking sequences that were cloned in a plasmid in stage a) of the method of the invention, will be the adjacent sequences, to the right and left of the concrete location of the bacterial genome in which the DNA fragment is to be interchanged, the sequences being cloned in such a way that said flanking sequences will be separated in the plasmid by the DNA fragment that is to be interchanged). In this case, the two sequences flanking the region of the bacterial genome that is to be substituted with a different DNA fragment will be cloned, in the plasmid of the invention with which the bacterium is subsequently transformed, in such a way that they are separated by the DNA fragment with which the region of the bacterial genome is to be substituted.

The method proves to be simple and inexpensive and makes it possible to construct bacterial strains with all the genetic modifications that are required, its only limitation being the negative effect on the viability of the bacterium caused by the mutations that are generated.

When the Gram-negative bacterium that is to be submitted to mutagenesis is sensitive to transduction by phages, the plasmid integrated in the genome (stage d) can be transferred to other strains by the process of horizontal transmission of DNA called generalized transduction, which consists of the transfer of DNA between bacteria with a phage as vector. The phage will transport, from the chromosome of the donor strain to the chromosome of the recipient strain, the DNA fragment that contains the integrated plasmid, avoiding stages b) and c) necessary for integration of the plasmid in the recipient strain. Then excision of the plasmid will be carried out by the process described in stage e).

In the case of *Salmonella*, lysates can be prepared from each of the strains with the integrated plasmid using the phage P22 following the protocol of Maloy et al. (Maloy et al., 1996). For other bacteria that are to be submitted to mutagenesis, it will be necessary to use a similar protocol with the appropriate phage that is able to produce lysates in them.

When modification of the genome is carried out using plasmids that contain, in addition to the indicator gene and the counterselection gene, a selection marker gene, selection of the bacteria transformed with the plasmid is more reliable. Hence, other preferred embodiments of the invention are those in which the plasmid in stage a) is a plasmid that additionally contains a selection gene, stage c) of selection of the strain transformed in stage b) is carried out using a culture medium that comprises the selection compound that eliminates the bacteria not transformed with the plasmid in stage a) and stage d) for selection of strains that have the plasmid inserted in their genome is carried out using a culture medium that comprises the same selection compound. As already mentioned, it is preferable for the selection marker gene to be a gene that confers resistance to an antibiotic. When the starting plasmid in stage a) is the plasmid pKO3blue, which contains a chloramphenicol resistance gene, stages c) and d) will be carried out in the presence of said antibiotic, chloramphenicol.

Regardless of whether or not use is made of selection by means of antibiotics or some other selection gene, if the plasmid used is the plasmid pKO3blue or any other plasmid that comprises lacZ as indicator gene, stage c) will be carried out by growing the bacteria on a culture plate, in the presence of X-Gal or by adding said compound once the colonies have grown, since it is the compound that gives rise to a reaction that indicates that the bacterium in which the blue colour is produced has been transformed with the plasmid of stage a). This will make it possible to select the bacteria that have been transformed with the plasmid, since they will be those that are coloured blue after incubation with X-Gal. Similarly, if the plasmid used is pKO3blue or some other plasmid that contains the heat-sensitive replication origin derived from the plasmid pSC101 (i.e. its replication origin is the replication origin derived from the plasmid pSC101, which can be regarded as heat-sensitive because the plasmid contains a gene that encodes a heat-sensitive protein essential for the initiation of replication, the heat-sensitive protein RepA), stage d) will be carried out at 43° C. or at a temperature higher than that, which does not cause the death of the bacterium, whereas stage a) will be carried out at between 25° C. and 35° C., preferably at 28-30° C. Finally, regarding the counterselection gene, when the plasmid contains the sacB gene, as is the case for the plasmid pKO3blue, stage e) will be carried out in a culture medium that contains sucrose, in such a way that the bacteria in which excision and loss of the plasmid has taken place, which will be those that are resistant to the presence of sucrose, survive.

In addition, it is advisable to incorporate a stage in which it is verified that the genome contains the desired modification. Thus, preference is given to those embodiments of the method of the invention that incorporate an additional stage f) in which it is verified, by amplification of the sequences and analysis of the products obtained by a method of sequence analysis (which can be sequencing proper or, where applicable, a method for verifying the size of the PCR products obtained, such as electrophoresis), that the genome contains the desired modification. In the case of making deletions or insertions of a size that is easily detectable by electrophoresis, such as that relating to fragments larger than 500 base pairs, simple electrophoresis of the PCR products in the presence of size markers can be sufficiently indicative that the desired deletion or insertion has taken place; in the case of point substitutions or interchange of sequences of similar size, it is preferable to have recourse to methods such as sequencing for verifying that the desired modification has taken place.

As has been mentioned, the modifications can consist of deletions, insertions or substitutions. The DNA fragment or fragments to be inserted into the plasmid of the invention in stage a) will be designed and obtained taking into account the modification that is to be made in the bacterial genome and the localization of the genome in which it is desired to produce said modification. In any case, so that the recombination event can take place, the DNA fragment that is to be modified in the genome must be cloned into the plasmid accompanied by the sequences flanking the region of the genome where the modification is to be introduced. If we wish to make a deletion, for example, the most practical way is to amplify the sequences flanking the fragment of the genome that we wish to remove from the bacterial chromosome, designing suitable primer pairs, and clone both flanking sequences, joined to one another, into the plasmid. Using a plasmid designed in this way, when the recombination event takes place and the subsequent excision of the plasmid, the excision can take place in such a way that the wild-type sequence is recovered or in such a way that the sequence between the two flanking sequences is removed, which requires a selection process for identifying the desired strain. Substitution of one sequence with another can be carried out similarly, by cloning, into the plasmid, the sequence with which we wish to interchange the target gene, flanked by two sequences homologous with the regions that flank the target gene that is to be substituted. For inserting a DNA fragment into the genome, said fragment will be cloned into the plasmid flanked by two sequence fragments that are adjacent to the point of insertion in the bacterial genome. FIG. 5 shows an example of amplification and cloning of the sequences flanking the target gene in the plasmid pKO3blue, to be used for producing the deletion of the gene located in the genome between the two flanking sequences, those between the primer pairs A/B and C/D. The recognition sites of the restriction enzymes will depend on each experiment, as well as the position of the oligonucleotides relative to the modification that we wish to introduce. If we wish to substitute a sequence of the genome with any other sequence, it will be possible to clone said other sequence between the two sequences already cloned in the plasmid that are flanking the region of the genome that we wish to substitute. If we wish to insert any DNA sequence into the genome, it will be possible to clone said sequence between the two sequences already cloned in the plasmid that are flanking the region of the genome into which we wish to insert said sequence.

Accordingly, the embodiments of the method of the present invention are preferred that comprise the stages, prior to each round of modification, of:

a) amplifying the fragments adjacent to the region of the chromosome that we wish to modify;
b) inserting both flanking sequences into a plasmid from any one of Claims 1 to 6 so that they are contiguous in the 5'-3' direction if we wish to make a deletion or are separated by the DNA fragment that is to be substituted or inserted into the bacterial genome.

It is preferable for the size of each of the amplified adjacent fragments to be at least 500 nucleotides, because homologous recombination is optimum with fragments of this size or larger. It is not advisable to use DNA fragments smaller than 250 nucleotides, because it reduces the efficiency of integration of the plasmid by homologous recombination.

Regardless of the method that is used for its production and the modification that is intended to be carried out, the transformation of the bacterium with the plasmid can be carried out by any method known by a person skilled in the art. Electroporation or heat shock is especially preferred.

Using the method of the invention, with which it is possible to perform multiple modifications in the genome of Gram-negative bacteria, the inventors constructed two strains of $S.$ $enteritidis$ in which the 12 genes that encode the GGDEF proteins that this bacterium possesses were deleted. The bacterium obtained was designated, generically, mutant $\Delta$XII; the specific mutants obtained were given the designations $\Delta$XII::Km and $\Delta$XII::Clo (in the case of the mutants having an antibiotic resistance gene) and DXII (in the case of the mutant lacking any antibiotic resistance gene). The $\Delta$XII mutant strains are unable to synthesize c-di-GMP (FIG. 7), and therefore the entire signalling cascade that depends on this secondary signal transmitter is absent from these bacteria. The $\Delta$XII mutants are completely avirulent (FIG. 8A), but are able to cross the epithelial barrier and invade the organs (FIGS. 8B and 8C), so it is an excellent candidate for the development of attenuated vaccines for immunization against infections by $Salmonella$ spp. or as a vector for expression of antigens of any organism (xenoantigens, including allergens and drugs), for immunoprophylactic or immunotherapeutic and therapeutic purposes. Particularly, mutant DXII lacks any exogenous DNA, either able to confer antibiotic resistance or of any other kind, a feature that makes it particularly convenient for being applied as an attenuated living vaccine, specially to human beings and other mammals, and that facilitates is authorization for that purpose, as it should not be considered a Genetically Modified Organism. Moreover, the particular DXII strain obtained as set forth in Example 6 of the present application, $\Delta$XII $\Delta$rpoS, additionally exhibits a deletion in a bacterial global regulator, namely factor sigma rpoS, an alternative transcription factor, which deletion renders the strain unable to form biofilms or cellulose, while remaining avirulent, what makes this particular strain even safer for being administered to humans and other mammals than the other ΔXII mutants.

Accordingly, another additional object of the invention comprises the mutant strains of *Salmonella* spp. in which all the genes that encode the GGDEF proteins have been deleted. In particular, a preferred embodiment of said mutants of the invention is that in which the mutant strain is a mutant strain of *Salmonella enterica Enteritidis* serotype in which the twelve genes that encode GGDEF proteins have been deleted. Particularly preferred embodiments of said object of the invention are the specific cases of mutant ΔXII, production of which is described later in the examples of the present specification, obtained from the clinical isolate 3934: the mutants ΔXII::Km and ΔXII::Clo and, very particularly, mutant ΔXII ΔrpoS.

Starting from these strains ΔXII::Km and ΔXII::Clo and from intermediate strains used for their construction, the inventors constructed two derived strains, each of which produces a single GGDEF protein, by reinsertion of the corresponding gene. In these two strains, the synthesis of c-di-GMP depends on a single GGDEF protein. These strains are of enormous value for searching for chemical molecules that interfere with or block the metabolism of c-di-GMP, affecting their viability, virulence, ability to form biofilm, and survival in the environment. Since c-di-GMP occurs exclusively in bacteria, any gene involved in its synthesis/degradation represents a potential target for the development of a new family of antimicrobials. Thus, another object of the invention comprises the strains of *Salmonella* spp. whose genome contains only one functional gene that encodes GGDEF proteins, as well as the intermediate strains that can be used for their production, i.e. the mutant strains of *Salmonella* spp. in which at least one of the genes that codes for GGDEF proteins has been deleted using the method of the invention. Among these, the strains derived from the *Enteritidis* serotype of *Salmonella enterica* (*S. enteritidis*) are preferred. In the case of the mutants that possess just one functional gene that expresses a GGDEF protein, they can be obtained from a ΔXII mutant strain (ΔXII::Km or ΔXII::Clo or, even, the DXII strain lacking antibiotic resistance genes) by reinserting in them the previously deleted gene of interest, or from any of the intermediate strains used for obtaining said mutant strains ΔXII, such as the strains ΔI, ΔII, ΔIII, ΔIV, ΔV, ΔVI, ΔVII, ΔVIII, ΔIX, ΔX or ΔXI that are described hereunder in the Examples of the present specification. ("Functional gene" means the gene that is capable of expressing the protein encoded in its sequence and that is capable of performing the recognized function for said protein in the same conditions in which it would have it in a wild-type *Salmonella* strain).

A further object of the present invention is the use of any of these strains (including the ΔXII mutant strains) for the development of vaccines or for the manufacture of medicinal products intended to be used as vaccines. In connection with said use, another object of the present invention is the use of said strains as vectors for expression of antigens of any organism (xenoantigens), which can be from other bacterial strains or from other organisms. The present invention also relates to the use of said strains as expression vectors of drugs.

As it is extremely useful in this field, yet another object of the present invention is the use of said mutant *Salmonella* strains for investigating the metabolism of c-di-GMP, with particular preference for those strains that express a single functional GGDEF protein. In particular, a specific use of the foregoing is application for the identification and development of chemical substances that block c-di-GMP synthesis. Finally, other uses of the mutant strains of the invention that constitute objects of the invention are application for investigating the mechanisms of formation and blocking of the formation of biofilms and/or of the relationship between biofilms and virulence.

The present invention will be explained in more detail with the figures and examples given below, in which the construction of a preferred embodiment of the plasmids of the invention, the plasmid pKO3blue, is described. This was used for practical application of the method of modification of the invention, firstly for providing two mutants that lack the 12 genes that encode GGDEF proteins (ΔXII::Km and ΔXII::Clo) for subsequently reinserting, in ΔXII::Km, independently, the genes previously deleted, or using ΔXII::Km for deleting the kanamycin resistance cassette (thus obtaining a strain with no antibiotic resistance and no exogenous DNA fragment) and the gene rpoS (thus obtaining an avirulent strain even more stable).

EXAMPLES

Figure 1:
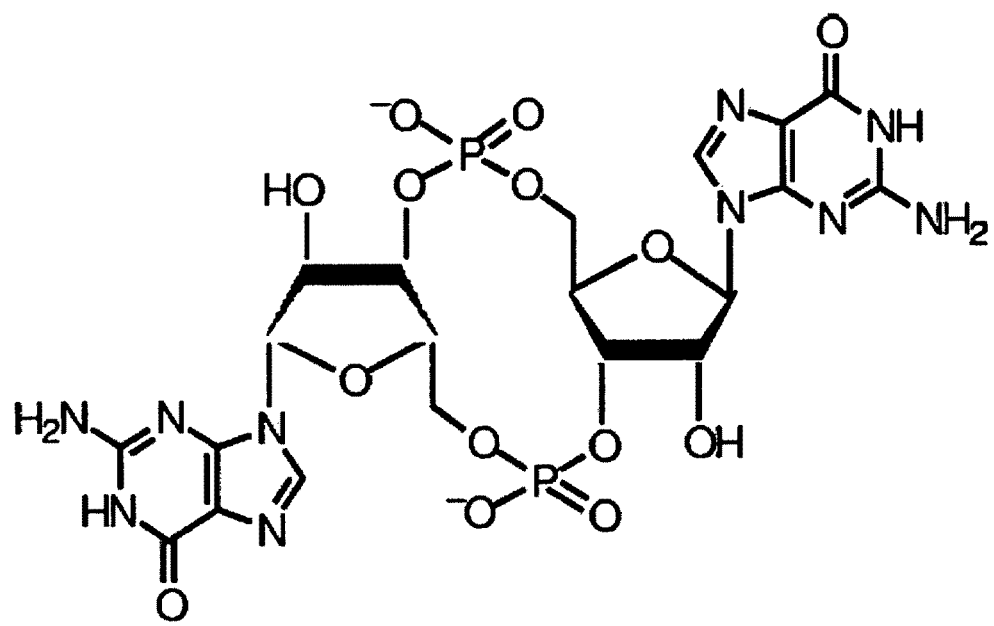
FIG. 1 shows the structure of c-di-GMP.
Figure 2:
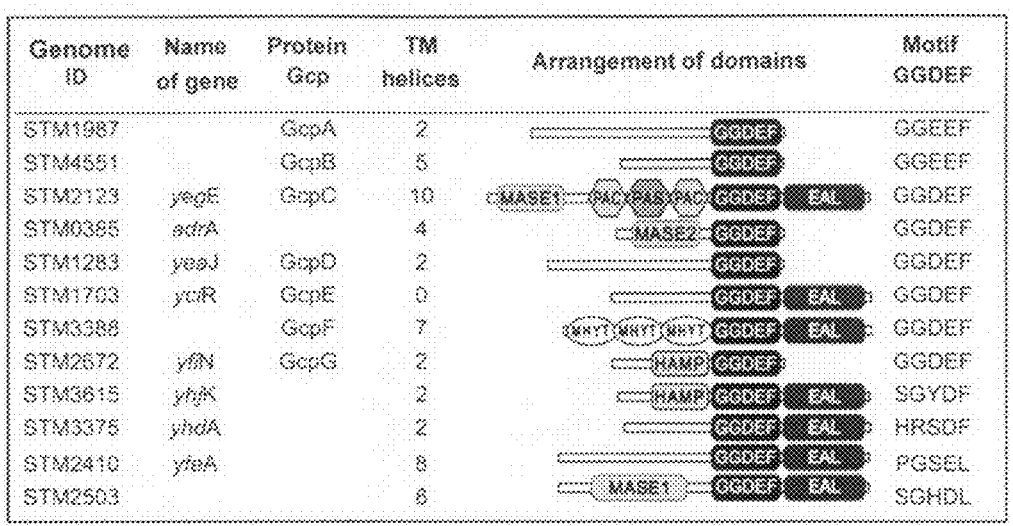
FIG. 2 shows, in part (A), the list of genes that encode proteins with the GGDEF domain in the genome of *S. enterica*. The table gives, in the first column, the number of the ORF (open reading frame) in the genome of *S. typhimurium* LT2, the name assigned to said gene (second column), the name of the protein (third column), the number of transmembrane helices (fourth column), the arrangement of known domains in these proteins is represented schematically (fifth column) and the conservation of the GGDEF motif in each of them is shown. Part (B) shows the position in kilobases of the 12 genes that encode proteins with the GGDEF domain in the genome of *S. typhimurium* LT2.
Figure 2:
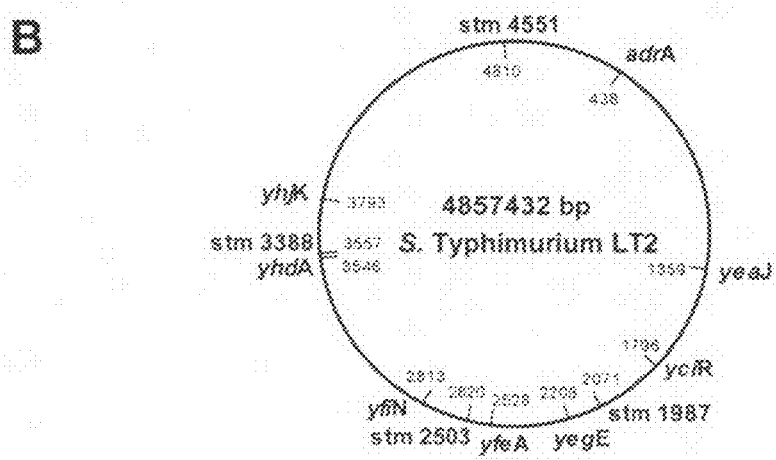
Figure 3:
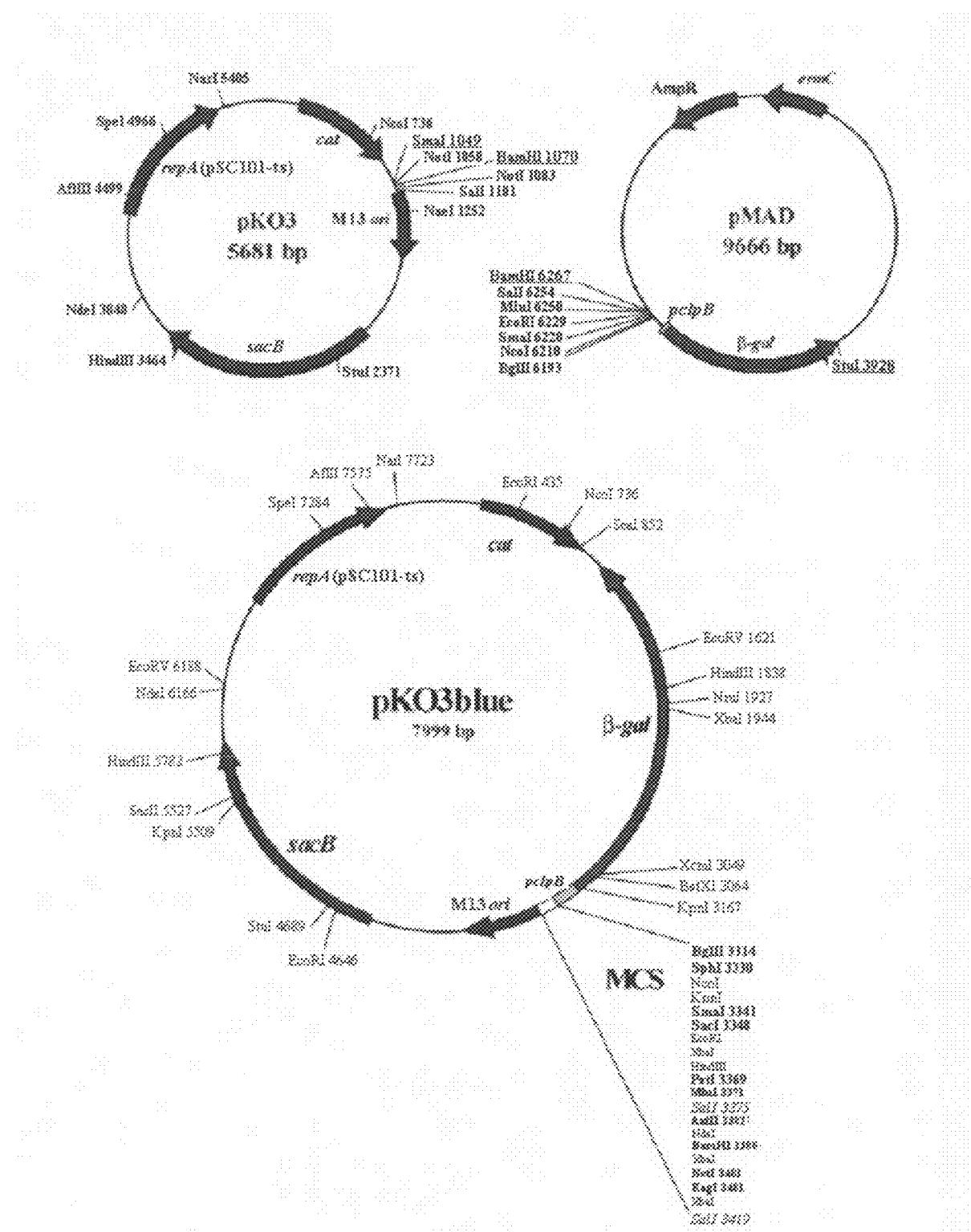
FIG. 3 shows the map of the plasmids pKO3 (plasmid at top left), pMAD (plasmid at top right) and pKO3blue (plasmid at the bottom). The underlined legends on the lines indicate the positions of the restriction enzymes used for introducing the β-galactosidase gene that contains the plasmid pMAD in the plasmid pKO3. The legends on the plasmids correspond to: repA: a gene that encodes a heat-sensitive protein essential for initiation of replication of the plasmid converting the replication origin (PSC101-ts: heat-sensitive replication origin derived from the plasmid pSC101) to heat-sensitive; cat chloramphenicol resistance gene; β-gal: lacZ gene that expresses β-galactosidase; sacB: gene that confers sensitivity to the presence of sucrose.

The present examples show the construction of the plasmid pKO3blue and the use thereof, in conjunction with the method of the invention, for making modifications in the genome of a Gram-negative bacterium, concretely, for obtaining strains of S. enteritidis.

Example 1

Construction of the Plasmid pKO3Blue

The plasmid was constructed by cloning a gene that codes for β-galactosidase into a plasmid that possesses a heat-sensitive replication origin (see FIG. 3). In this case, the β-galactosidase gene of *Bacillus stearothermophilus* obtained from the plasmid pMAD was cloned into the plasmid pKO3 (Link et al., 1997). For this, the plasmid pMAD (Arnaud et al., 2004), which contains the sequence that encodes β-galactosidase under the promoter pclpB, was digested with BamHI/StuI and the β-galactosidase gene was cloned between the BamHI/SmaI restriction sites of the plasmid pKO3.

To facilitate amplification of this plasmid, the *E. coli* strain XL1Blue was transformed by electroporation with the recombinant plasmid obtained, obtaining the *Escherichia coli* strain XL1Blue pKO3blue, which was deposited in the Spanish Type Culture Collection, being assigned the accession number CECT 7241, as reflected in the section "Deposition of Microorganisms".

Any other plasmid containing a heat-sensitive replication origin and some other indicator gene could be used for the same purpose.

Example 2

Production of the Recombinant Plasmid with which the Bacteria are Transformed

To obtain the plasmid with which the bacteria are to be transformed, two DNA fragments of approximately 500 nucleotides whose sequence corresponded, in each case, to the regions adjacent to the region of the chromosome that we wish to modify (see FIG. 5), were cloned into the resultant plasmid, pKO3blue. These fragments were obtained by amplification by PCR using the pairs of nucleotides NB and C/D applicable in each case, depending on the gene that we wished to delete. A and B form a pair of primers that make it possible to amplify one of the flanking regions of the gene that is to be removed, whereas C and D form a second pair of primers that make it possible to amplify the flanking region located at the opposite end of the gene that is to be deleted. Amplification will be carried out in such a way that on fusing both fragments in the plasmid, this will produce the modification that we wish to introduce into the chromosome of the bacterium: substitution, deletion or insertion of a sequence. In the case of construction of the mutant ΔXII::Km and of the mutant ΔXII::Clo, all the desired modifications consisted of deletion of genes, concretely, those of the GGDEF family. Thus, the desired modification in each of the 12 rounds of modification carried out was deletion of the sequence fragment located in the genome between the flanking regions AB and CD. Each of the GGDEF genes was deleted completely from the translation start codon (ATG or GTG) to the translation stop codon and 6 nucleotides of the sequence in front of the start codon and behind the stop codon were also deleted and substituted with the sequence of an XhoI target (incorporated in the corresponding oligos B and C). The gene yeaJ was deleted by recombination with a linear DNA fragment by introducing an antibiotic resistance cassette by the method of Datsenko and Wanner (Datsenko & Wanner, 2000). On the one hand a fragment of the gene yeaJ was deleted by the insertion of a kanamycin cassette, obtaining the mutant ΔXII::Km, and on the other hand the gene yeaJ was deleted completely from the start codon to the stop codon by introducing a chloramphenicol resistance cassette, obtaining the mutant ΔXII::Clo.

The oligonucleotides used as primers in the amplification of the fragments in each of the deleted genes, and the oligonucleotides used for mutating the gene yeaJ by the method of Datsenko & Wanner, are shown below in Table 1.

TABLE 1

Oligonucleotides used for performing the deletion of each of the genes that encode the GGDEF proteins of *S. enteritidis*

| Genome ID/ Gene size (nt) | Gene name | Oligonucleotides | Pairing points of the oligonucleotides (nt)* | Size of the amplified fragments (nt) |
|---|---|---|---|---|
| STM0385 | adrA | A: 01-A (SEQ ID NO: 1) | −610 | AB: 618 |
| 1113 nt | | B: 01-B (SEQ ID NO: 2) | −6 | CD: 505 |
| | | C: 01-C (SEQ ID NO: 3) | +6 | |
| | | D: 01-D (SEQ ID NO: 4) | +499 | |
| STM1283 | yeaJ | A: YeaJ-Km Fw (SEQ ID NO: 7) | 1000 | |
| 1494 nt | | B: YeaJ-Km Rv (SEQ ID NO: 8) | 1494 | |
| | | C: 02 Clo-Fw (SEQ ID NO: 9) | 1 | |
| | | D: 02 Clo-Rv (SEQ ID NO: 10) | 1494 | |
| STM1703 | yciR | A: 03-A (SEQ ID NO: 13) | −620 | AB: 628 |
| 1983 nt | | B: 03-B (SEQ ID NO: 14) | −6 | CD: 483 |
| | | C: 03-C (SEQ ID NO: 15) | +6 | |
| | | D: 03-D (SEQ ID NO: 16) | +477 | |
| STM1987 | | A: 04-A (SEQ ID NO: 19) | −608 | AB: 616 |
| 1713 nt | | B: 04-B (SEQ ID NO: 20) | −6 | CD: 513 |
| | | C: 04-C (SEQ ID NO: 21) | +6 | |
| | | D: 04-D (SEQ ID NO: 22) | +507 | |
| STM2123 | yegE | A: 05-A (SEQ ID NO: 25) | −610 | AB: 618 |
| 2991 nt | | B: 05-B (SEQ ID NO: 26) | −6 | CD: 504 |
| | | C: 05-C (SEQ ID NO: 27) | +6 | |
| | | D: 05-D (SEQ ID NO: 28) | +498 | |
| STM2410 | yfeA | A: 06-A (SEQ ID NO: 31) | −625 | AB: 633 |

TABLE 1-continued

Oligonucleotides used for performing the deletion of each of the genes that encode the GGDEF proteins of S. enteritidis

| Genome ID/<br>Gene size<br>(nt) | Gene<br>name | Oligonucleotides | Pairing points<br>of the<br>oligonucleotides<br>(nt)* | Size of the<br>amplified<br>fragments<br>(nt) |
|---|---|---|---|---|
| 2190 nt | | B: 06-B (SEQ ID NO: 32) | −6 | CD: 472 |
| | | C: 06-C (SEQ ID NO: 33) | +6 | |
| | | D: 06-D (SEQ ID NO: 34) | +466 | |
| STM2672<br>1221 nt | yfiN | A: 07-A (SEQ ID NO: 39)<br>B: 07-B (SEQ ID NO: 40)<br>C: 07-C (SEQ ID NO: 41)<br>D: 07-D (SEQ ID NO: 42) | −598<br>−6<br>+6<br>+488 | AB: 606<br>CD: 494 |
| STM3375<br>1941 nt | yhdA | A: 08-A (SEQ ID NO: 45)<br>B: 08-B (SEQ ID NO: 46)<br>C: 08-C (SEQ ID NO: 47)<br>D: 08-D (SEQ ID NO: 48) | −603<br>−6<br>+6<br>+516 | AB: 611<br>CD: 522 |
| STM3388<br>2100 nt | | A: 09-A (SEQ ID NO: 51)<br>B: 09-B (SEQ ID NO: 52)<br>C: 09-C (SEQ ID NO: 53)<br>D: 09-D (SEQ ID NO: 54) | −609<br>−6<br>+6<br>+508 | AB: 617<br>CD: 516 |
| STM3615<br>1974 nt | yhjK | A: 10-A (SEQ ID NO: 57)<br>B: 10-B (SEQ ID NO: 58)<br>C: 10-C (SEQ ID NO: 59)<br>D: 10-D (SEQ ID NO: 60) | −607<br>−6<br>+6<br>+496 | AB: 615<br>CD: 502 |
| STM4551<br>1065 nt | | A: 11-A (SEQ ID NO: 63)<br>B: 11-B (SEQ ID NO: 64)<br>C: 11-C (SEQ ID NO: 65)<br>D: 11-D (SEQ ID NO: 66) | −617<br>−6<br>+6<br>+553 | AB: 625<br>CD: 561 |
| STM2503<br>2214 nt | | A: 12-A (SEQ ID NO: 69)<br>B: 12-B (SEQ ID NO: 70)<br>C: 12-C (SEQ ID NO: 71)<br>D: 12-D (SEQ ID NO: 72) | −610<br>−6<br>+6<br>+506 | AB: 618<br>CD: 512 |

*The number refers to the localization of the first nucleotide of the 5' end of the oligonucleotide. The minus sign signifies that the pairing sequence of the oligonucleotide is before the start codon and the plus sign that it is behind the stop codon. If there is no sign, this indicates that the pairing sequence of the oligonucleotide is in the coding region, 1 being considered the first nucleotide of the start codon of the gene coding region.

The conditions of the PCR reactions for amplifying the regions AB and CD and to verify cloning of the fragments AB and CD in the plasmid pGEMt-easy were as follows:

30 cycles {
Denaturation: 5 minutes at 94° C.
Denaturation: 45 seconds at 94° C.
Hybridization of the primers: 1 minute at 54° C.
Extension: 45 seconds at 72° C.
Final extension: 10 minutes at 72° C.
}

The DNA fragments obtained by amplification by PCR using the corresponding pairs of oligonucleotides A/B and C/D were cloned into the plasmid pGEMt-easy. The plasmid that contained the amplification product obtained with the oligonucleotides A/B was digested with the restriction enzymes NotI-XhoI and the plasmid containing the amplification product obtained with the oligonucleotides C/D was digested with the restriction enzymes XhoI-BglII. The digestion products were resolved in agarose gels and the fragments AB and CD were purified from agarose gel using a commercial kit.

The purified fragments were ligated simultaneously with the plasmid pKO3blue digested with the enzymes NotI-BglII and the E. coli strain XL1Blue was transformed by electroporation with the recombinant plasmid obtained.

The transformants obtained are analysed by PCR using as primers the pair formed by A and D and the following conditions:

30 cycles {
Denaturation: 5 minutes at 94° C.
Denaturation: 45 seconds at 94° C.
Hybridization of the primers: 1 minute at 54° C.
Extension: 90 seconds at 72° C.
Final extension: 10 minutes at 72° C.
}

Then the plasmid was purified from a positive clone.

Example 3

Use of the Method of Chromosomal Modification for Deleting Genes that Encode Proteins with the GGDEF Domain in the Genome of S. enteritidis 3934

The plasmid pKO3blue obtained in Example 2 containing the fragments AB and CD was introduced by electroporation into the strain S. enteritidis 3934 (deposited in the Spanish Type Culture Collection (CECT) with the accession number CECT 7236) and the electroporated bacteria were incubated for 4 h at 28° C. in liquid medium, then they were seeded on plates with a culture medium containing chloramphenicol (20 µg/ml), and X-gal (5-bromo-4-chloro-3-indolyl-beta-D-galactopyranoside) (40 µg/ml) and were incubated at 28° C. for 72 h. The transformed strain of S. enteritidis was selected as a blue colony (see FIG. 4).

Figure 5:
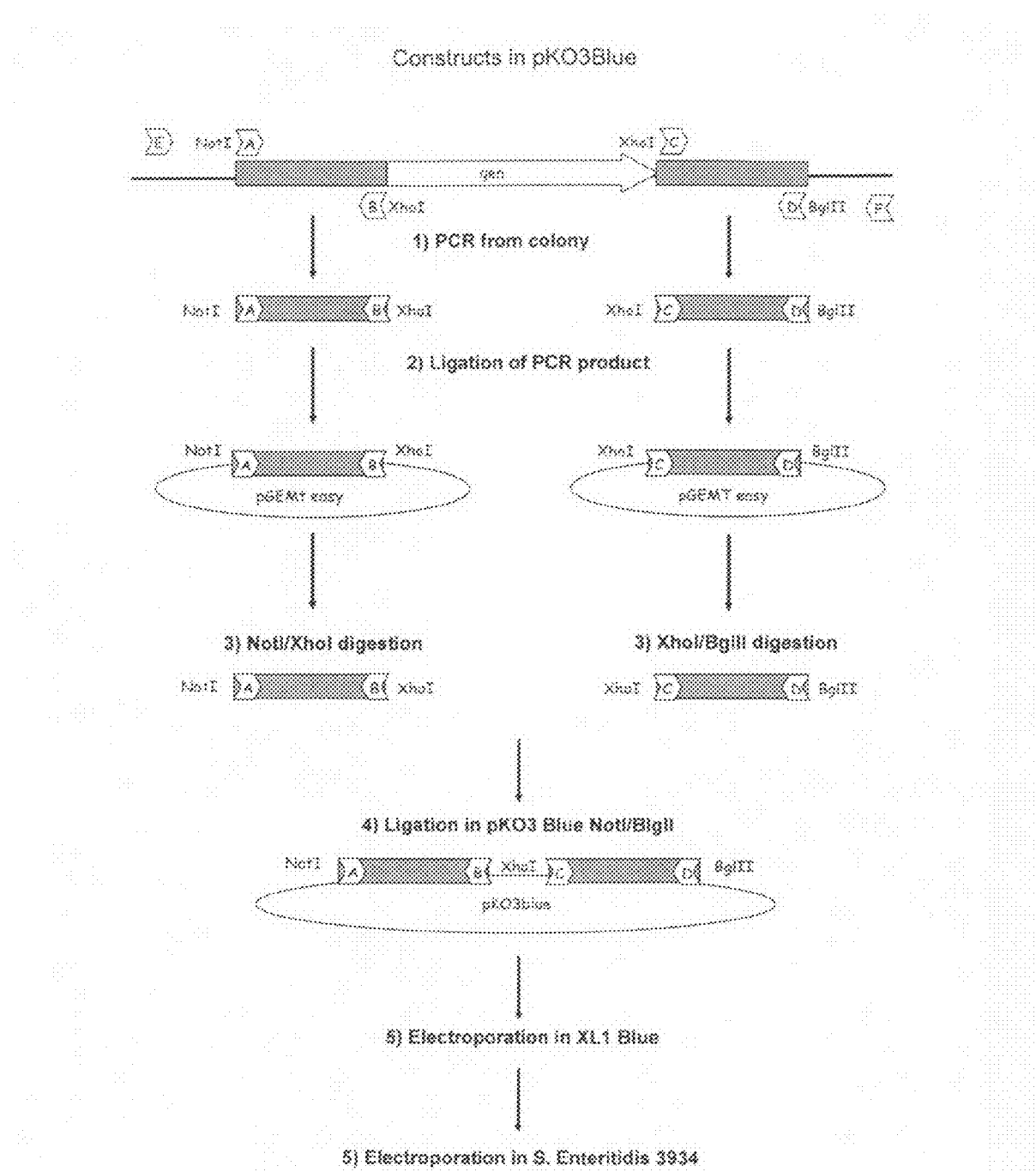
FIG. 5 shows an example of the experimental design used for preparing the modification that we wish to insert into the genome of the bacterium and its cloning into the plasmid pKO3blue. The regions flanking the gene that we wish to delete is amplified by PCR using the oligonucleotides A, B, C and D. The amplified fragments are digested with restriction enzymes whose sequence has been introduced into the sequence of the oligonucleotides B and C (XhoI) and are cloned into the plasmid pKO3blue using the enzymes that digest in the oligonucleotides A (NotI) and D (BglII).

Once selected, the strain was inoculated in liquid medium preheated to 43° C. containing chloramphenicol (20 µg/ml) and was incubated at 43° C. for 48 h to permit integration of the plasmid into the chromosome of the bacterium by a process of homologous recombination (recombination of the Campbell type). Since the plasmid has a heat-sensitive replication origin, it is unable to multiply at 43° C. and only those bacteria that integrate the plasmid into the chromosome will be able to grow in the presence of chloramphenicol at 43° C. 75 μl of the culture was plated by exhaustion in streaks on a plate preheated to 43° C. that contained a culture medium with chloramphenicol (20 μg/ml) and X-gal (40 μg/ml) and was incubated at 43° C. for 48 hours. After incubation, from six to nine colonies (depending on the gene) were selected, in which the plasmid had possibly been integrated (blue colonies) and were replicated on plates preheated to 43° C. that contained a culture medium with chloramphenicol (20 μg/ml) and X-gal (40 μg/ml) and incubated at 43° C. for 48 hours. The colonies that had incorporated the plasmid into the genome showed a blue colour owing to constitutive expression of the β-galactosidase gene. Integration of the plasmid was verified by PCR using the oligos A and F (see FIG. 5), and using the following PCR conditions for amplifying the chromosome region between the oligos A and F:

30 cycles
- Denaturation: 5 minutes at 94° C.
- Denaturation: 45 seconds at 94° C.
- Hybridization of the primers: 1 minute at 54° C.
- Extension: from 2.5 minutes to 3.5 minutes at 72° C. (depending on the protein to be analysed)
- Final extension: 10 minutes at 72° C.

Those that did not display amplification and which therefore carried the integrated plasmid, were selected. The strains with the integrated plasmid were stored in glycerol at −80° C.

Starting from two that were integrated (blue colonies) the excision process was begun, incubating them in liquid medium without antibiotic at 28° C. for 24 hours. In this stage, as a result of a second recombination process, in a percentage of the population there will be excision of the plasmid, with loss of resistance to chloramphenicol and β-galactosidase activity. Dilutions of the culture were seeded on culture plates containing X-gal and sucrose (5%), and the plates were incubated for 24 hours at 28° C.

A number of white colonies (for example 24) were selected and were plated on culture plates with chloramphenicol (20 μg/ml) and on culture plates containing X-gal and sucrose (5%). The chloramphenicol-sensitive colonies were selected and, for these colonies, a PCR was carried out using the oligonucleotides E and F (see FIG. 5) and with the following conditions in the PCR reactions:

30 cycles
- Denaturation: 5 minutes at 94° C.
- Denaturation: 45 seconds at 94° C.
- Hybridization of the primers: 1 minute at 54° C.
- Extension: from 2.5 minutes to 4.5 minutes at 72° C. (depending on the protein to be analysed)
- Final extension: 10 minutes at 72° C.

Figure 4:
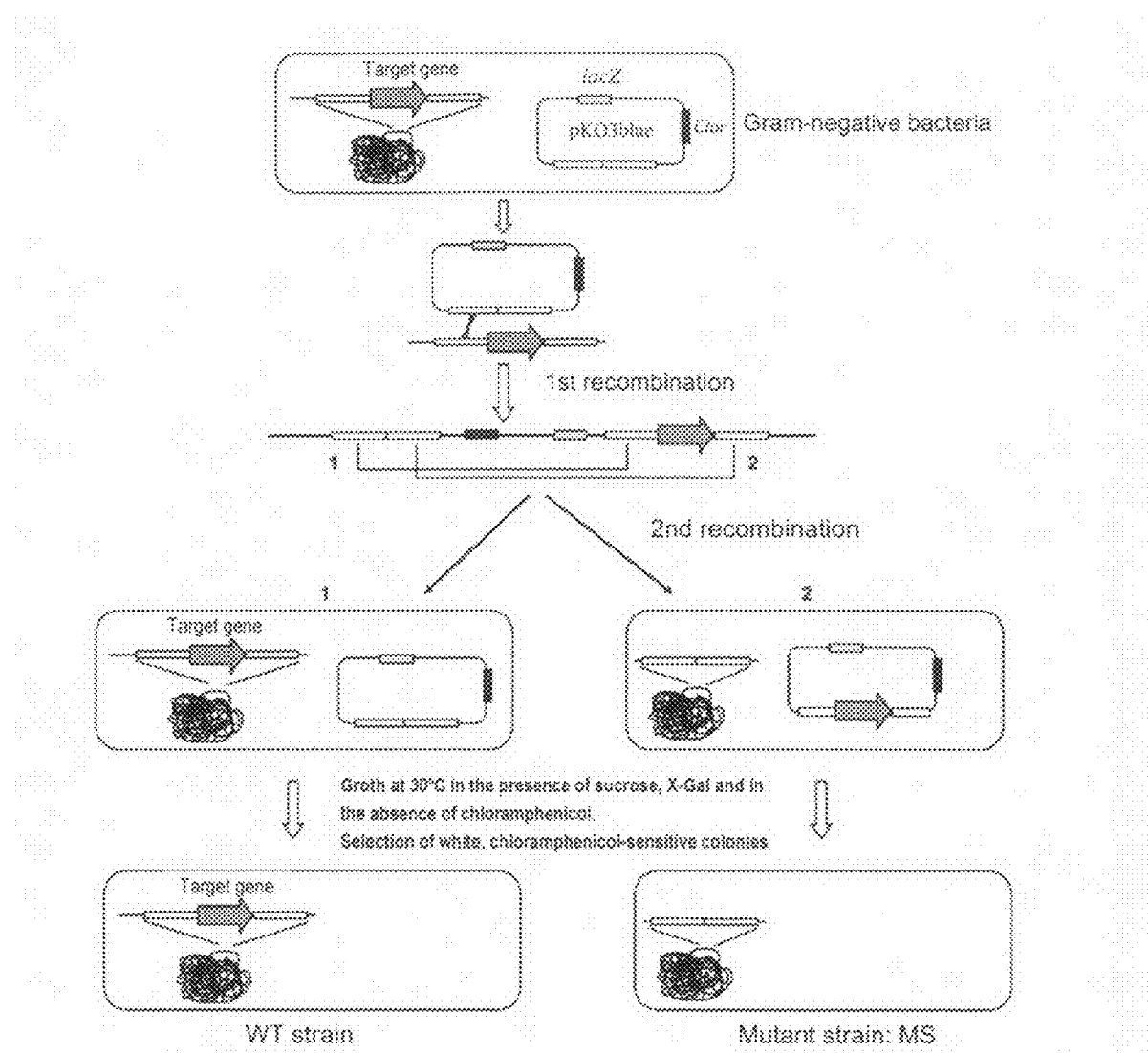
FIG. 4 shows the process of allelic interchange by double recombination used for introducing the modification of the genome of the Gram-negative bacterium that we wish to modify. For this, in a first homologous recombination, the plasmid pKO3blue is inserted into the genome of the Gram-negative bacterium (1st recombination) and then it is split (2nd recombination) to generate the original wild-type strain or the recombinant strain that contains the desired modification. Growth in the presence of the counterselection compound, at the permissive temperature, makes it possible to identify the bacteria that contain the desired modification: (WT: recombinant strain identical to the original wild-type strain; MS: mutant strain that contains the desired modification).

The size of the fragment obtained in the amplification makes it possible to identify those colonies that have incorporated the desired mutation into the chromosome (drawing in FIG. 4, bottom right) and reject those colonies in which, after the second recombination, they recover the wild-type copy of the gene (drawing in FIG. 4, bottom left). The PCR product is digested with the enzyme XhoI and in addition it is sequenced to guarantee its specificity.

The oligonucleotides E and F used for each deleted gene and the size of the fragments amplified by them are shown in Table 2:

TABLE 2

Oligonucleotides E and F used for verifying the state of the GGDEF genes in the intermediate mutants with deletions in said genes and in the mutants ΔXII::Km and ΔXII::Clo.

| Genome ID | Name of the gene | Oligonucleotides E F | Size of the PCR product: wild-type strain/mutant XII | Size of the products of digestion of the PCR product of the mutant XII with the enzyme XhoI |
|---|---|---|---|---|
| STM0385 | adrA | 01-E (SEQ ID NO: 5) 01-F (SEQ ID NO: 6) | 2427 pb/1310 pb | 745 pb/565 pb |
| STM1283 | yeaJ | yeaJ Fw (SEQ ID NO: 11), yeaJ Rv (SEQ ID NO: 12) | 2379 pb/3338 pb (Km) 2379 pb/1899 pb (Clo) | / / |
| STM1703 | yciR | 03-E (SEQ ID NO: 17) 03-F (SEQ ID NO: 18) | 3375 pb/1386 pb | 711 pb/675 pb |
| STM1987 | | 04-E (SEQ ID NO: 23) 04-F (SEQ ID NO: 24) | 2998 pb/1279 pb | 716 pb/563 pb |
| STM2123 | yegE | 05-E (SEQ ID NO: 29) 05-F (SEQ ID NO: 30) | 4317 pb/1320 pb | 722 pb/598 pb |
| STM2410 | yfeA | 06-E (SEQ ID NO: 35) 06-F (SEQ ID NO: 36) | 3520 pb/1324 pb | 715 pb/609 pb |
| STM2672 | yfiN | 07-E (SEQ ID NO: 43) 07-F (SEQ ID NO: 44) | 2602 pb/1375 pb | 717 pb/658 pb |
| STM3375 | yhdA | 08-E (SEQ ID NO: 49) 08-F (SEQ ID NO: 50) | 3281 pb/1334 pb | 717 pb/617 pb |
| STM3388 | | 09-E (SEQ ID NO: 55) 09-F (SEQ ID NQ: 56) | 3448 pb/1342 pb | 730 pb/612 pb |
| STM3615 | yhjK | 10-E (SEQ ID NO: 61) 10-F (SEQ ID NO: 62) | 3378 pb/1398 pb | 709 pb/689 pb |
| STM4551 | | 11-E (SEQ ID NO: 67) 11-F (SEQ ID NO: 68) | 2468 pb/1398 pb | 717 pb/681 pb |
| STM2503 | | 12-E (SEQ ID NO: 73) 12-F (SEQ ID NO: 74) | 3519 pb/1300 pb | 717 pb/583 pb |

Once the modification introduced into the chromosome of the strain has been confirmed by PCR, digestion of the PCR product and sequencing of the PCR product, the process can be repeated as many times as desired. For making modifications on genes whose alteration can affect the heat sensitivity of the host bacterium, it will be possible to change the temperatures for each of the stages.

This method was followed, firstly, for producing a deletion in the gene adrA (stm0385). After that, deletions were produced in the genes stm1987, yciR, yegE, yfiN, yhdA, stm3388, yhjK, stm4551, yfeA and stm2503. In this way, a collection of individual mutants was generated, in which deletions were produced in each of the genes that encode GGDEF proteins in the genome of S. enteritidis.

As already mentioned, to achieve sequential mutation of several genes, and if the Gram-negative strain that is to be submitted to mutagenesis is sensitive to transduction by phages, the following method can be used: When constructing the strains in which each of the target genes has been deleted/inserted/altered individually using the process described previously, the strains in which the plasmid pKO3blue is integrated in these target genes can be stored in glycerol at −80° C. These strains must be incubated at 43° C., in the presence of chloramphenicol, to prevent the plasmid splitting. Starting from an individual mutant in a gene A, a process of transduction is carried out using a lysate obtained from a strain that contains the plasmid pKO3blue integrated into one of the target genes, for example gene B. The phage transports the integrated plasmid together with the flanking region of the chromosome and, by homologous recombination of the flanking regions, the plasmid is integrated into the strain in which mutation of gene A was carried out previously, then proceeding to modification of gene B. Next, excision of the plasmid is carried out by the process described previously. In this way, a double mutant is obtained in genes A and B. This process can be repeated sequentially as many times as desired and in the order that is desired.

In this example, to achieve the sequential mutation of each of the genes that encode these proteins, the following method was followed: Once deletion of the gene stm0385 (adrA) was confirmed, this strain was submitted to a process of transduction using a lysate of phage P22 obtained from the strain that contains the plasmid pKO3blue integrated into the gene stm1987. Next, excision of the plasmid was carried out by the process described previously. In this way a double mutant was obtained in the genes adrA and stm1987. This process was repeated sequentially with each of the genes yciR, yegE, yhdA, stm3388, yhjK, stm4551, yfeA and stm2503. The gene yeaJ was deleted by recombination with a linear DNA fragment by introducing a cassette for resistance to kanamycin or to chloramphenicol by the method of Datsenko and Wanner (Datsenko & Wanner, 2000) and in this way the two strains that lack the twelve genes that encode proteins with the GGDEF domain: ΔXII::Km and ΔXII::Clo, respectively, were obtained. In this process, together with the complete mutant, a collection of intermediate strains is generated, characterized by successively lacking a gene that encodes a GGDEF protein:

ΔI: *S. enteritidis* 3934 ΔadrA
ΔII: *S. enteritidis* 3934 ΔadrA Δstm1987
ΔIII: *S. enteritidis* 3934 ΔadrA Δstm1987 ΔyeaJ::Km
ΔIV: *S. enteritidis* 3934 ΔadrA Δstm1987 ΔyeaJ::Km ΔyciR
ΔV: *S. enteritidis* 3934 ΔadrA Δstm1987 ΔyeaJ::Km ΔyciR ΔyegE
ΔVI: *S. enteritidis* 3934 ΔadrA Δstm1987 ΔyeaJ::Km ΔyciR ΔyegE ΔyfiN
ΔVII: *S. enteritidis* 3934 ΔadrA Δstm1987 ΔyeaJ::Km ΔyciR ΔyegE ΔyfiN ΔyhdA
ΔVIII: *S. enteritidis* 3934 ΔadrA Δstm1987 ΔyeaJ::Km ΔyciR ΔyegE ΔyfiN ΔyhdA Δstm3388
ΔIX: *S. enteritidis* 3934 ΔadrA Δstm1987 ΔyeaJ::Km ΔyciR ΔyegE ΔyfiN ΔyhdA Δstm3388 ΔyhjK
ΔX: *S. enteritidis* 3934 ΔadrA Δstm1987 ΔyeaJ::Km ΔyciR ΔyegE ΔyfiN ΔyhdA Δstm3388 ΔyhjK Δstm4551
ΔXI: *S. enteritidis* 3934 ΔadrA Δstm1987 ΔyeaJ::Km ΔyciR ΔyegE ΔyfiN ΔyhdA Δstm3388 ΔyhjK Δstm4551 ΔyfeA
ΔXII::Km: *S. enteritidis* 3934 ΔadrA Δstm1987 ΔyeaJ::Km ΔyciR ΔyegE ΔyfiN ΔyhdA Δstm3388 ΔyhjK Δstm4551 ΔyfeA Δstm2503
ΔXII::Clo: *S. enteritidis* 3934 ΔadrA Δstm1987 ΔyeaJ::Clo ΔyciR ΔyegE ΔyfiN ΔyhdA Δstm3388 ΔyhjK Δstm4551 ΔyfeA Δstm2503

Absence of the genes that encode the GGDEF proteins was confirmed by Southern blot (FIG. 10). The chromosomal DNA of the mutant ΔXII::Km was purified, digested with the restriction enzymes PstI and SalI, submitted to agarose gel electrophoresis and transferred to a nylon membrane using already established methods (Ausubel et al., 1990). Fragments of each of the genes that encode the corresponding GGDEF proteins that were amplified with the oligos presented in Table 3 were used as probes, with the following PCR conditions:

| | |
|---|---|
| 30 cycles | Denaturation: 5 minutes at 94° C.<br>Denaturation: 45 seconds at 94° C.<br>Hybridization of the primers: 1 minute at 52° C.<br>Extension: 45 seconds at 72° C.<br>Final extension: 10 minutes at 72° C. |

Labelling of the probes and hybridization of the DNA were carried out according to the protocol supplied with the *PCR-DIG DNA-Labelling and Chemiluminiscent Detection Kit* (Boehringer Mannheim).

Absence of the genes that encode the GGDEF proteins was also confirmed by PCR using the oligonucleotides E and F of the flanking regions of each of the genes, as explained previously.

TABLE 3

Oligonucleotides used for generating the fragments of the GGDEF genes that were used as probes in Southern Blotting.

| Genome ID | Gene Name | Oligonucleotides | Size of the amplified fragment (nt) |
|---|---|---|---|
| STM0385 | adrA | adrA int.Fw (SEQ ID NO: 77)<br>adrA int.Rv (SEQ ID NO: 78) | 421 |
| STM1283 | yeaJ | yeaJ int.Fw (SEQ ID NO: 79)<br>yeaJ int.Rv (SEQ ID NO. 80) | 270 |
| STM1703 | yciR | yciR int.Fw (SEQ ID NO: 81)<br>yciR int.Rv (SEQ ID NO: 82) | 576 |
| STM1987 | | DGC II.Fw (SEQ ID NO: 83)<br>DGC III.Rv (SEQ ID NO: 84) | 639 |
| STM2123 | yegE | yegE VI.Fw (SEQ ID NO: 85)<br>yegE V.Rv (SEQ ID NO: 86) | 621 |
| STM2410 | yfeA | yfeA probe Fw (SEQ ID NO: 87)<br>yfeA probe Rv (SEQ ID NO: 88) | 507 |
| STM2672 | yfiN | yfiN III.Fw (SEQ ID NO: 89)<br>yfiN III.Rv (SEQ ID NO: 90) | 427 |
| STM3375 | yhdA | yhdA int.Fw (SEQ ID NO: 91)<br>yhdA int.Rv (SEQ ID NO: 92) | 558 |
| STM3388 | | stm3388 IV.Fw (SEQ ID NO: 93)<br>stm3388 V.Rv (SEQ ID NO: 94) | 483 |

TABLE 3-continued Oligonucleotides used for generating the fragments of the GGDEF genes that were used as probes in Southern Blotting.

| Genome ID | Gene Name | Oligonucleotides | Size of the amplified fragment (nt) |
|---|---|---|---|
| STM3615 | yhjK | yhjK int.Fw (SEQ ID NO: 95) yhjK int.Rv (SEQ ID NO: 96) | 610 |
| STM4551 | | stm4551 III.Fw (SEQ ID NO: 97) stm4551 II.Rv (SEQ ID NO: 98) | 626 |
| STM2503 | | stm2503 int.Fw (SEQ ID NO: 99) stm2503 int.Rv (SEQ ID NO: 100) | 495 |

The mutant strain ΔXII::Km or ΔXII::Clo can be distinguished from any other strain by the PCR described previously, using the oligonucleotides E and F, which hybridize in the flanking regions of each of the genes, and digestion with the restriction enzyme XhoI. The size of the DNA fragments resulting from the amplification reaction and digestion with XhoI for each gene is as shown in Table 2.

This process can be used for deleting the gene sequence as desired, and in the desired order, with the sole limitation that the effect of the deletion can have on the viability of the bacterium.

Figure 7:
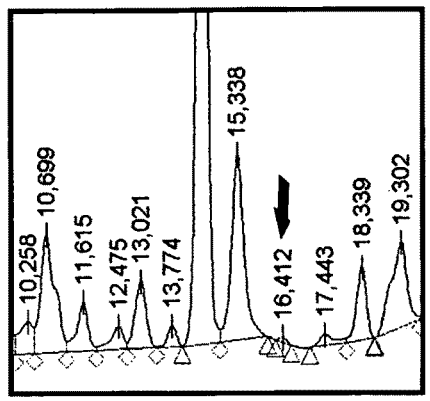
FIG. 7 shows the levels of c-di-GMP according to HPLC in the wild-type strain (*S. enteritidis* 3934) (top diagrams) and the mutant ΔXII::Km (bottom diagrams). The diagrams on the right correspond to samples in which c-di-GMP was injected to check the localization of the peak corresponding to this compound. It can be seen that the wild-type strain accumulates an amount of c-di-GMP of 1.46 pmol/mg after 24 hours of incubation on plates of LB without salt at 28° C. Note that the levels of c-di-GMP in ΔXII::Km are not detectable. The results represent the mean value of three independent experiments.
Figure 7:
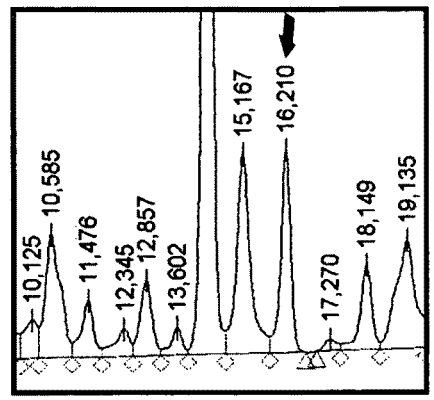
Figure 7:
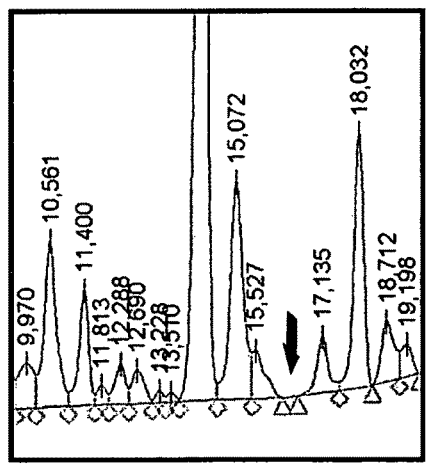
Figure 7:
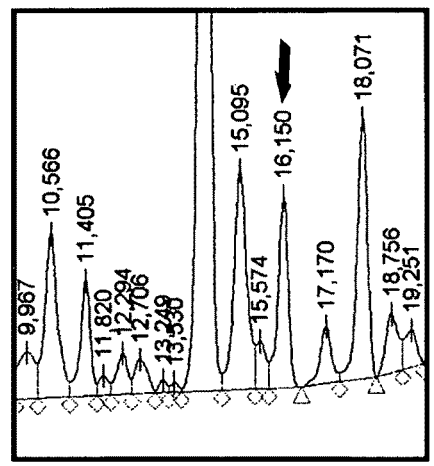

Once the process is completed, it can be seen that the strain lacking the complete family of GGDEF proteins ΔXII::Km:

Does not have detectable levels of c-di-GMP measured by HPLC and mass spectrometry, as can be seen from FIG. 7, which shows the levels of c-di-GMP found by HPLC in the wild-type strain (S. enteritidis 3934) and the mutant ΔXII::Km. The wild-type strain accumulates an amount of c-di-GMP of 1.46 pmol/mg after 24 hours of incubation on plates of LB without salt at 28° C. Note that the levels of c-di-GMP in ΔXII::Km are not detectable. The results represent the mean value of three independent experiments. The samples were analysed using a Waters 2695 Alliance HPLC system and were injected in a reverse-phase column $100C_{18}$ 10 μm 25×0.46 and a precolumn $WP300C_{18}$. The column was eluted at a flow rate of 1 ml/min using a gradient from 0% to 15% of B in 30 minutes (A, ammonium acetate; B, acetonitrile:water (1:1)).

Figure 6:
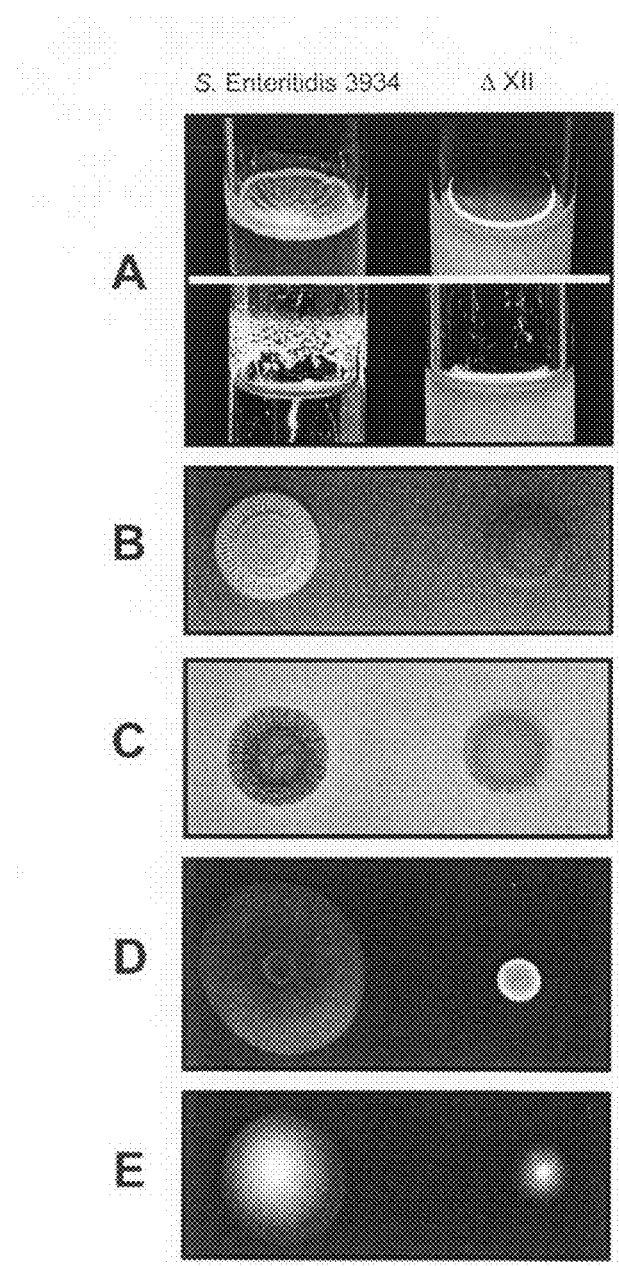
FIG. 6 (A) shows the biofilm-forming capacity of the mutant ΔXII::Km (part on the right of the photographs, headed "ΔXII") versus that of the parent strain (part on the left of the photographs, headed "S. enteritidis 3934"). In the Luria Bertani (LB) rich medium (top photo) the parent strain forms a biofilm as a film at the medium-air interface after 72 hours of incubation at room temperature and in static conditions. The parent strain is also capable of forming a biofilm as a ring adhering to the glass in the nutrient-deficient medium designated ATM (bottom photo of part A) in which the bacterium is unable to multiply and in which an optical density of 0.4 measured at 590 nm is inoculated and is incubated for 4 hours at 37° C. with vigorous stirring. As can be seen, the mutant ΔXII::Km was unable to form biofilm in both media. Part (B) shows the capacity of the mutant ΔXII::Km for synthesizing cellulose, revealed on calcofluor plates. Both the parent strain and ΔXII::Km were incubated for 48 h at room temperature on an LB plate to which calcofluor was added (200 μg ml$^{-1}$). Calcofluor is a fluorochrome that can bind to the β-glucoside bonds present in cellulose, one of the components of the exopolysaccharide matrix making up the biofilm of *Salmonella*, in such a way that the colonies of the strains capable of producing cellulose appear fluorescent when observed under UV light of 360 nm. In contrast to the parent strain, ΔXII::Km was unable to produce cellulose. Part (C) shows the capacity of the mutant ΔXII::Km for synthesizing cellulose and fimbriae of the curli type on visualizing the colony morphology on plates with Congo Red. Both the parent strain and ΔXII::Km were incubated for 48 h at 28° C. on plates of LB without salt, supplemented with Congo Red (40 μg ml$^{-1}$) and Coomassie Brilliant Blue (20 μg ml$^{-1}$) and the colony morphology was analysed. Several colony morphotypes were established in this medium in relation to the capacity for producing cellulose and fimbriae of the curli type, both essential components of the biofilm in *Salmonella*. When the strain is able to synthesize cellulose and fimbriae of the curli type the colonies appear red and rough (morphotype rdar: red, dry and rough), if the strain is unable to synthesize cellulose but can synthesize fimbriae of the curli type the morphotype is bdar (brown, dry and rough), if the strain is unable to synthesize fimbriae of the curli type but is capable of producing cellulose the morphotype is pdar (pink, dry and rough) and finally, if the strain is unable to synthesize both cellulose and fimbriae of the curli type the morphotype is saw (smooth and white). The mutant ΔXII::Km presented a saw morphotype, compared with the rdar morphotype of the parent strain, which revealed the inability of ΔXII::Km to produce cellulose and fimbriae of the curli type. Part (D) and (E) show the analysis of mobility in the mutant ΔXII::Km. *Salmonella* is able to move on the surface of a solid medium (swarming) (part D). To investigate this capacity, 5 μl of a culture ON at 37° C. of the parent strain and of the mutant ΔXII::Km was inoculated on an LB plate with 0.5% of agar and 0.5% of glucose and was incubated ON at room temperature. In contrast to the parent strain the mutant ΔXII::Km was not capable of moving on the surface. *Salmonella* is also capable of swimming within a semisolid medium (swimming) (part E). To investigate this ability, 5 μl of a culture ON at 37° C. of the parent strain and of the mutant ΔXII::Km was inoculated on an LB plate with 0.3% of agar and was incubated ON at room temperature. In contrast to the parent strain, the mutant ΔXII::Km was not capable of moving within the medium.

The mutant ΔXII::Km is immobile, lacks formation of biofilm, and lacks synthesis of cellulose and of fimbriae of the curli type. This can be verified in FIG. 6, which compares the behaviour of the wild-type strain S. enteritidis 3934 (left part of the photos of series A to E) with that of the mutant strain ΔXII::Km (right part of the photos of series A to E).

Figure 8:
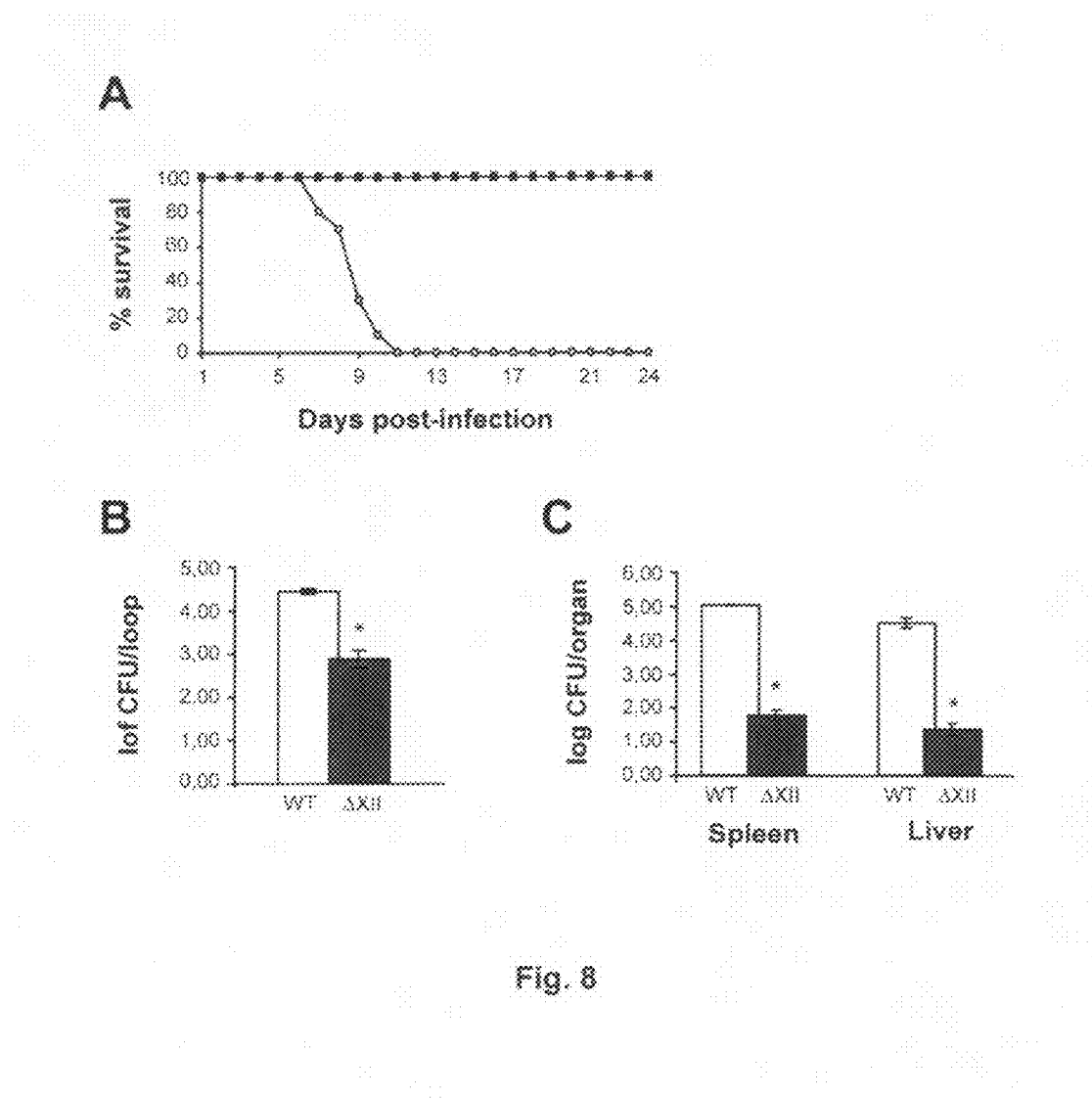
FIG. 8 shows the investigation of virulence of the mutant bacterium ΔXII::Km. Part (A) shows the investigation of survival. The ordinate shows the percentage of BALB/c mice, infected orally with $10^9$ CFU (colony-forming units) of the wild-type strain 3934 (open circles, ○) or of the mutant strain ΔXII::Km (filled squares, ■) that survive after the number of days post-infection shown on the abscissa. Note that all the mice infected with the wild-type strain die before day 12 post-infection, whereas none of the mice infected by the strain ΔXII::Km dies. Part (B) shows the intestinal loop test, which shows the logarithm to base 10 of the number of colony-forming units detected per loop (log ugcs/loop) after performing, on three mice, ligature of a fragment of small intestine that contains one or more Peyer's patches, inoculating an amount of $10^7$ CFU, incubating for 90 minutes, sacrificing the animal, cutting the piece of intestine between the two ligatures, and analysing the quantity of bacteria that have been able to cross the intestinal barrier and colonize the cells of the epithelium: the unshaded bar corresponds to the wild-type strain 3934 (WT), whereas the dark-shaded bar corresponds to the mutant strain ΔXII::Km (ΔXII). Part (C) shows a diagram corresponding to the organ colonization test, in which the ordinate shows the logarithm to base 10 of the number of colony-forming units detected per organ (log CFU/organ) after oral inoculation of 5 BALB/c mice with a sublethal dose of $10^4$ CFU and sacrificing the animal after 5 days of infection and quantifying the quantity of CFU in the spleen (first pair of bars) and the liver (second pair of bars). As in the previous case, the unshaded bar corresponds to the wild-type strain 3934 (WT), whereas the dark-shaded bar corresponds to the mutant strain ΔXII::Km (ΔXII).

The mutant ΔXII::Km is avirulent. Studies of virulence in BALB/c mice, in which $10^9$ bacteria were inoculated orally in female BALB/c mice weighing 20 g, showed that the mutant ΔXII::Km is avirulent (see FIG. 8). In part (A), batches of BALB/c mice were infected orally with $10^9$ CFU (colony-forming units) and the number of animals that survived after 24 days post-infection was determined. All the mice infected with the wild-type strain died before day 12 post-infection, whereas none of the mice infected with the strain ΔXII::Km died. Part (B) shows the intestinal loop test, in which ligature of the small intestine of approximately 1 cm was performed on anaesthetized mice, an amount of $10^7$ CFU was inoculated and incubated for 90 minutes. After incubation, the animal was sacrificed, the piece of intestine between the two ligatures was cut out and the quantity of bacteria that had been able to cross the intestinal barrier and colonize the cells of the epithelium was analysed, it being less in the case of the mutant ΔXII::Km (shaded bar), but close to $10^3$ CFU per loop. Part (C) corresponds to the organ colonization test; for this, 5 BALB/c mice were inoculated orally with a sublethal dose of $10^4$ CFU and after 5 days of infection the animals were sacrificed and the quantity of CFU in target organs such as spleen and liver was quantified; both in the liver and in the spleen, the number of bacteria detected was more their 3 orders of magnitude lower in the case of the mutant ΔXII::Km (shaded bars) compared with the wild-type strain (unshaded bars).

Example 4

Use of the Method of Chromosomal Modification for Inserting Genes that Encode Proteins with the GGDEF Domain in the Genome of S. enteritidis 3934 ΔXII::Km Another application of the method of modification of the invention is the insertion of genes or any DNA fragment into the chromosome of a bacterium by a process of homologous recombination.

A representative example is the insertion of the genes stm1987 and stm4551 into the genome of mutant bacteria generated in the preceding example, to obtain the strains *S. enteritidis* 3934 ΔXII+stm1987, *S. enteritidis* 3934 ΔXII+stm4551.

For the first of these, to obtain them, the gene stm1987 was inserted following the same method described for deleting genes in the preceding section, but varying the amplification primers and the fragment inserted into the plasmid pKO3blue: the gene stm1987 was amplified using the pair of oligonucleotides 04-A (SEQ ID NO:19) and 04-D (SEQ ID NO:22) and the following PCR conditions:

| | |
|---|---|
| 30 cycles | Denaturation: 5 minutes at 94° C.<br>Denaturation: 45 seconds at 94° C.<br>Hybridization of the primers: 1 minute at 54° C.<br>Extension: 3 minutes at 72° C.<br>Final extension: 10 minutes at 72° C. | and was cloned into the plasmid pGEMt-easy. This plasmid was digested with the restriction enzymes NotI-BglII. The digestion product was resolved in agarose gels and the fragment containing the stm1987 gene as well as the DNA regions adjacent to said gene (2816 pb) was purified from an agarose gel using a commercial kit. The purified fragment was ligated into the plasmid pKO3blue, digested with the enzymes NotI-BglII and the *E. coli* strain XL1Blue was transformed by electroporation. The transformants obtained were analysed by PCR using the oligos 04-A (SEQ ID NO:19) and 04-D (SEQ ID NO:22) and the PCR conditions described previously and the plasmid of a positive clone was purified. This plasmid was introduced by electroporation into the strain *S. enteritidis* 3934 ΔXII::Km. The strain of *S. enteritidis* 3934 ΔXII::Km transformed was selected as a blue colony on plates with a culture medium containing chloramphenicol (20 μg/ml) and X-gal (5-bromo-4-chloro-3-indolyl-beta-D-galactopyranoside) (40 μg/ml) at 28° C.

Once selected, the strain was incubated at 43° C. in liquid medium in the presence of chloramphenicol (20 μg/ml) for 48 hours to permit integration of the plasmid into the chromosome of the bacterium by a process of homologous recombination (recombination of the Campbell type). Since the plasmid has a heat-sensitive replication origin, it is not able to multiply at 43° C. and only those bacteria that integrate the plasmid into the chromosome will be able to grow in the presence of chloramphenicol at 43° C. 75 µl of the culture was plated on a plate preheated to 43° C. that contained a culture medium with chloramphenicol (20 µg/ml) and X-gal (40 µg/ml) and was incubated at 43° C. for 48 hours. After incubation, six colonies in which the plasmid was possibly integrated (blue colonies) were selected, and were replicated on plates preheated to 43° C. that contained a culture medium with chloramphenicol (20 µg/ml) and X-gal (40 µg/ml) and were incubated at 43° C. for 48 hours. The colonies that had incorporated the plasmid into the genome were coloured blue owing to constitutive expression of the β-galactosidase gene.

After incubation, starting from two that were integrated (blue colonies) the process of excision was begun, incubating in liquid medium without antibiotic at 28° C. for 24 hours. In this stage, as a result of a second recombination process, in a percentage of the population there will be excision of the plasmid, with loss of resistance to chloramphenicol and β-galactosidase activity. Dilutions of the culture were seeded on culture plates containing X-gal and sucrose (5%), and the plates were incubated for 24 h at 28° C.

24 white colonies were selected for performing PCR using the oligonucleotides 04-E (SEQ ID NO:23) and 04-F (SEQ ID NO:24) and the following conditions:

| 30 cycles | Denaturation: 5 minutes at 94° C.<br>Denaturation: 45 seconds at 94° C.<br>Hybridization of the primers: 1 minute at 54° C.<br>Extension: 3 minutes at 72° C.<br>Final extension: 10 minutes at 72° C. |
|---|---|

The size of the fragment obtained in the amplification made it possible to identify those colonies that had recovered the stm1987 gene in the chromosome and reject those colonies in which, after the second recombination, the deletion present in the ΔXII::Km had been recovered. Insertion of the stm1987 gene was confirmed by amplification of the stm1987 gene using the oligonucleotides 04-E (SEQ ID NO:23) and 04-F (SEQ ID NO:24) and the PCR conditions described previously, and the specificity of the amplification product of the PCR reaction was determined by sequencing the PCR product.

This same process was also carried out with another 8 genes that encode GGDEF proteins of *S. enteritidis*: adrA, yeaJ, yciR, yegE, yfiN, yhdA, stm3388, yhjK, using in each case the corresponding oligonucleotides, as described in Tables 1 and 2. Note that in the case of the yeaJ gene, the pair of oligonucleotides 02-H (SEQ ID NO:75) and 02-I (SEQ ID NO:76) was used. The strain *S. enteritidis* 3934 ΔXII+stm4551 was constructed from the intermediate mutant ΔIX (*S. enteritidis* 3934 ΔadrA Δstm1987 ΔyeaJ::Km ΔyciR ΔyegE ΔyfiN ΔyhdA Δstm3388 ΔyhjK) in which the stm2503 gene was deleted using the method described in this invention and in which the yfeA gene was then mutated by the insertion of a chloramphenicol cassette using Datsenko's method and the oligonucleotides 06-Clo Fw (SEQ ID NO:37) and 06-Clo Rv (SEQ ID NO:38). In this way the strain *S. enteritidis* 3934 ΔadrA Δstm1987 ΔyeaJ::Km ΔyciR ΔyegE ΔyfiN ΔyhdA Δstm3388 ΔyhjK Δstm2503 ΔyfeA-Clo was obtained, which has been designated *S. enteritidis* 3934 ΔXII+stm4551 and which only produces a single GGDEF protein.

The strain *S. enteritidis* 3934 ΔXII+yfeA was constructed from the intermediate mutant ΔX (*S. enteritidis* 3934 ΔadrA Δstm1987 ΔyeaJ-Km ΔyciR ΔyegE ΔyfiN ΔyhdA Δstm3388 ΔyhjK Δstm4551) in which the stm2503 gene was deleted using the method described in this invention. In this way the strain *S. enteritidis* 3934 ΔadrA Δstm1987 ΔyeaJ-Km ΔyciR ΔyegE ΔyfiN ΔyhdA Δstm3388 ΔyhjK Δstm4551 Δstm2503 was obtained, which has been designated *S. enteritidis* 3934 ΔXII+yfeA and which only produces a single GGDEF protein.

The strain *S. enteritidis* 3934 ΔXII+stm2503 was constructed from the intermediate mutant ΔX (*S. enteritidis* 3934 ΔadrA Δstm1987 ΔyeaJ-Km ΔyciR ΔyegE ΔyfiN ΔyhdA Δstm3388 ΔyhjK Δstm4551) in which the yfeA gene was deleted using the method described in this invention. In this way the strain *S. enteritidis* 3934 ΔadrA Δstm1987 ΔyeaJ-Km ΔyciR ΔyegE ΔyfiN ΔyhdA Δstm3388 ΔyhjK Δstm4551 ΔyfeA was obtained, which has been designated *S. enteritidis* 3934 ΔXII+stm2503 and which only produces a single GGDEF protein.

In this way a collection of 12 strains was generated, characterized in that they each produce a single GGDEF protein:
  *Salmonella enteritidis* 3934 ΔXII+stm1987
  *Salmonella enteritidis* 3934 ΔXII+stm4551
  *Salmonella enteritidis* 3934 ΔXII+adrA
  *Salmonella enteritidis* 3934 ΔXII+yeaJ
  *Salmonella enteritidis* 3934 ΔXII+yciR
  *Salmonella enteritidis* 3934 ΔXII+yegE
  *Salmonella enteritidis* 3934 ΔXII+yfeA
  *Salmonella enteritidis* 3934 ΔXII+yfiN
  *Salmonella enteritidis* 3934 ΔXII+yhdA
  *Salmonella enteritidis* 3934 ΔXII+stm3388
  *Salmonella enteritidis* 3934 ΔXII+yhjK
  *Salmonella enteritidis* 3934 ΔXII+stm2503

Insertion of DNA fragments into the chromosome of any Gram-negative bacterium can be carried out following the method similar to that described in this example.

Example 5

Use of the Strain *S. enteritidis* 3934 ΔXII+stm4551 for the Identification of Chemical Substances that Inhibit c-di-GMP Synthesis All c-di-GMP that is able to synthesize the strain *S. enteritidis* 3934 ΔXII+stm4551 depends on the presence of the protein STM4551. The production of c-di-GMP by this protein activates the expression of concrete genes that have been identified by experiments using microarrays. One of the genes whose expression is activated with greater intensity in the presence of stm4551 is the csgA gene. This gene was substituted with the indicator gene lacZ, although it could be substituted with any other indicator gene (gus, GFP). The strain *S. enteritidis* 3934 ΔXII+stm4551 in which the csgA gene has been substituted with lacZ has levels of β-galactosidase activity measured according to Miller's method modified by Maloy (Maloy et al., 1996) of 400 units, when the strain is grown in wells of an ELISA plate in LB medium after incubation for 24 hours at 28° C.

When the strain *S. enteritidis* 3934 ΔXII+stm4551 is supplemented with a plasmid that overproduces the yciR gene, which encodes a protein with phosphodiesterase activity, capable of degrading c-di-GMP, the levels of β-galactosidase activity fall to values of 20 units, when the strain is grown in wells of an ELISA plate in LB medium after 24 hours of incubation at 28° C.

To determine whether a particular chemical compound is capable of interfering with c-di-GMP, different concentrations of this compound are added to the wells of an ELISA plate in which the control strain has been inoculated. To verify that the compound does not affect the growth of the bacterium, the growth of the bacterium is measured by reading the optical density at 600 nm. The compounds that affect the growth of the bacterium are rejected, and for those compounds that do not affect growth, the β-galactosidase activity is measured by the method described by Griffith et al. (Griffith & Wolf, 2002). Those substances whose presence blocks the transcription of the indicator gene and, consequently, the activity of the protein expressed by said gene, will be possible candidates for the development of drugs that block c-di-GMP.

Figure 9:
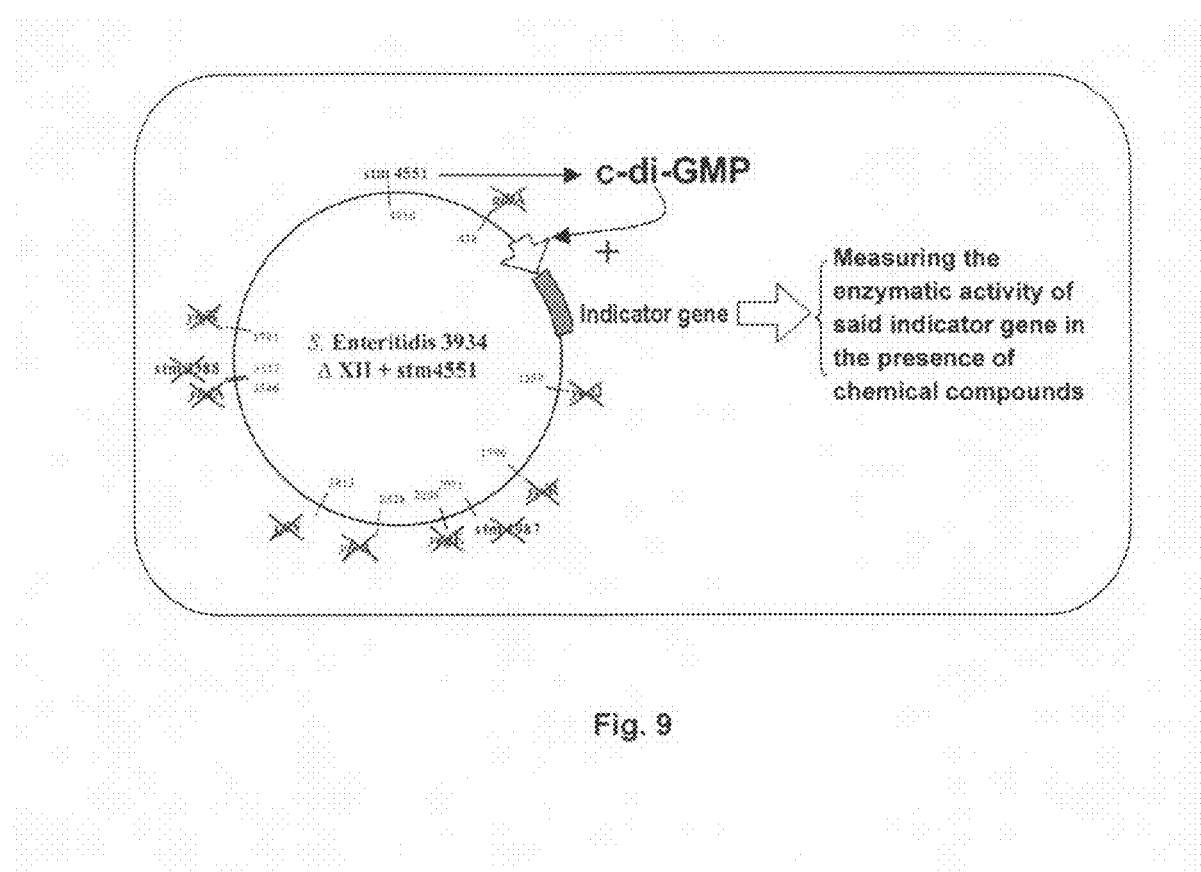
FIG. 9 shows a schematic representation of the genome of the mutant strain *S. enteritidis* 3934 ΔXII+stm4551 in which the csgA gene has been substituted with an indicator gene for carrying out tests for identification of substances that inhibit c-di-GMP synthesis by measuring the enzymatic activity of said indicator gene in the presence of the chemical under test. The genes crossed-out are the genes deleted in said strain.
Figure 10:
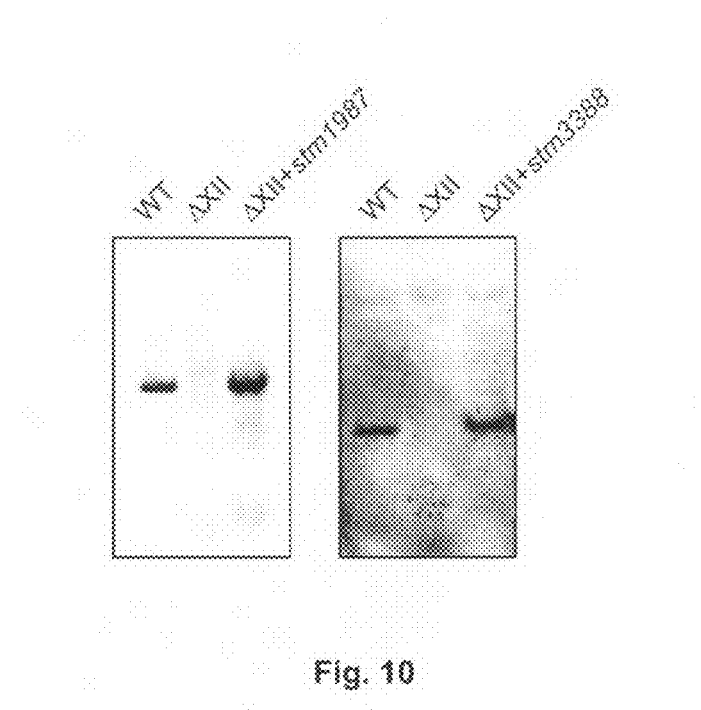
FIG. 10 shows Southern Blots performed to verify the deletion of two of the GGDEF genes (the genes stm1987 and stm3388) in the mutant ΔXII::Km. DNA from the parent strain was run in the first lane, which has a band corresponding to hybridization of the probe with the gene stm1987 (photograph on left) and the gene stm3388 (photograph on right) respectively. The second lane corresponds to the mutant ΔXII::Km, in which the gene, with which the probe used hybridizes, has been deleted, so that the probes are not able to hybridize and finally the third lane corresponds to the strains ΔXII+stm1987 and ΔXII+stm3388 respectively, in which it is demonstrated that the presence of these genes has been restored in the genome of these strains. The same results were observed in the Southern Blots that were performed for each of the 12 GGDEF genes.

FIG. 9 refers to the structure of the genome of the strain S. enteritidis 3934 ΔXII+stm4551 in which the csgA gene has been substituted with lacZ, valid for the identification of chemical substances that inhibit c-di-GMP synthesis.

Example 6

Use of the Method of Chromosomal Modification for Deleting the Cassette of Resistance of Kanamycin from the Genome of Strain S. enteritidis 3934 ΔXII::Km and Deleting Gene rpoS The strain S. enteritidis 3934 ΔXII::Km obtained as described in Example 3 was used to delete the kanamycin resistance cassette and the gene rpoS from its genome, following the method of modification of the invention. Particularly, the same procedure as described in Examples 2 and 3 was used.

The oligonucleotides used as primers in the amplification of the fragments AB and CD, used in the deletion of each gene, are shown below in Table 4.

The conditions of the PCR reactions for amplifying the regions AB and CD and to verify cloning of the fragments AB and CD in the plasmid pGEMt-easy were as follows:

| 30 cycles | Denaturation: 5 minutes at 94° C. |
| | Denaturation: 45 seconds at 94° C. |
| | Hybridization of the primers: 1 minute at 54° C. |
| | Extension: 1 minute at 72° C. |
| | Final extension: 10 minutes at 72° C. |

The DNA fragments obtained by amplification by PCR using the corresponding pairs of oligonucleotides A/B and C/D were cloned into the plasmid pGEMt-easy. The plasmid that contained the amplification product obtained with the oligonucleotides A/B was digested with the restriction enzymes NotI-XhoI and the plasmid containing the amplification product obtained with the oligonucleotides C/D was digested with the restriction enzymes XhoI-BglII. The digestion products were resolved in agarose gels and the fragments AB and CD were purified from agarose gel using a commercial kit.

The purified fragments were ligated simultaneously with the plasmid pKO3blue digested with the enzymes NotI-BglII and the E. coli strain XL1Blue was transformed by electroporation with the recombinant plasmid obtained.

The transformants obtained were analysed by PCR using as primers the pair formed by A and D and the following conditions:

| 30 cycles | Denaturation: 5 minutes at 94° C. |
| | Denaturation: 45 seconds at 94° C. |
| | Hybridization of the primers: 1 minute at 54° C. |
| | Extension: 1 minute 30 seconds at 72° C. |
| | Final extension: 10 minutes at 72° C. |

Then the plasmid was purified from a positive clone.

The pKO3blue-derived plasmid obtained, containing the fragments AB and CD, was introduced by electroporation into the strain S. enteritidis 3934 ΔXII::Km and the electroporated bacteria were incubated for 4 h at 28° C. in liquid medium, then they were seeded on plates with a culture medium containing chloramphenicol (20 μg/ml), and X-gal (5-bromo-4-chloro-3-indolyl-beta-D-galactopyranoside) (40 μg/ml) and were incubated at 28° C. for 72 h. The transformed strain was selected as a blue colony (see FIG. 4).

Once selected, the strain was inoculated in liquid medium preheated to 43° C. containing chloramphenicol (20 μg/ml) and was incubated at 43° C. for 48 h to permit integration of the plasmid into the chromosome of the bacterium by a process of homologous recombination (recombination of the Campbell type). As previously explained, since the plasmid has a heat-sensitive replication origin, it is unable to multiply at 43° C. and only those bacteria that integrate the plasmid into the chromosome will be able to grow in the presence of chloramphenicol at 43° C. 75 μl of the culture was plated by

TABLE 4

Oligonucleotides used for performing the deletion of the kanamycin resistance cassette and the gene rpoS from the genome of S. enteritidis 3934 ΔXII::Km

| Genome ID/<br>Gene size (nt) | Gene name | Oligonucleotides | Pairing points of the oligonucleotides (nt)* | Size of the amplified fragments (nt) |
|---|---|---|---|---|
| STM1283::Km$^R$<br>2453 nt | yeaJ::Km$^R$ | A: 02-E (SEQ ID NO: 101)<br>B: 02-J (SEQ ID NO: 102)<br>C: 02-C (SEQ ID NO: 103)<br>D: 02-D (SEQ ID NO: 104) | −720<br>21<br>+6<br>+517 | AB: 741<br><br>CD: 511 |
| STM2924<br>993 nt | rpoS | A: rpoS_1-Fw (SEQ ID NO: 107)<br>B: rpoS-B (SEQ ID NO: 108)<br>C: rpoS-C (SEQ ID NO: 109)<br>D: rpoS-D (SEQ ID NO: 110) | −899<br>−6<br>+6<br>+546 | AB: 892<br><br>CD: 540 |

*The number refers to the localization of the first nucleotide of the 5' end of the oligonucleotide. The minus sign signifies that the pairing sequence of the oligonucleotide is before the start codon and the plus sign that it is behind the stop codon. If there is no sign, this indicates that the pairing sequence of the oligonucleotide is in the coding region, 1 being considered the first nucleotide of the start codon of the gene coding region.

exhaustion in streaks on a plate preheated to 43° C. that contained a culture medium with chloramphenicol (20 µg/ml) and X-gal (40 µg/ml) and was incubated at 43° C. for 48 hours. After incubation, from six to nine colonies (depending on the gene) were selected, in which the plasmid had possibly been integrated (blue colonies) and were replicated on plates preheated to 43° C. that contained a culture medium with chloramphenicol (20 µg/ml) and X-gal (40 µg/ml) and incubated at 43° C. for 48 hours. The colonies that had incorporated the plasmid into the genome showed a blue colour owing to constitutive expression of the β-galactosidase gene. Integration of the plasmid was verified by PCR using the The size of the fragment obtained in the amplification makes it possible to identify those colonies that have incorporated the desired mutation into the chromosome (drawing in FIG. 4, bottom right) and reject those colonies in which, after the second recombination, they recover the wild-type copy of the gene (drawing in FIG. 4, bottom left). The PCR product is digested with the enzyme XhoI and in addition it was sequenced to guarantee its specificity.

The oligonucleotides E and F used for each deleted gene and the size of the fragments amplified by them are shown in Table 5:

TABLE 5

Oligonucleotides E and F used for verifying the state of the genes to be deleted in the mutant strain

| Genome ID | Name of the gene | Oligonucleotides E F | Size of the PCR product: Strain ΔXII::Km/ strain ΔXII ΔrpoS | Size of the products of digestion of the PCR product of the strain ΔXII ΔrpoS with the enzyme XhoI |
|---|---|---|---|---|
| STM1238::Km$^R$ | adrA | E: 02-K (SEQ ID NO: 111)<br>F: 02-F (SEQ ID NO: 112) | 3818 pb/1384 pb | 784 pb/600 pb |
| STM2924 | rpoS | E: rpoS-E (SEQ ID NO: 113)<br>F: rpoS-F (SEQ ID NO: 114) | 2642 pb/1643 pb | 983 pb/660 pb | oligos A and F (see FIG. 5), and using the following PCR conditions for amplifying the chromosome region between the oligos A and F:

30 cycles {
Denaturation: 5 minutes at 94° C.
Denaturation: 45 seconds at 94° C.
Hybridization of the primers: 1 minute at 54° C.
Extension: 3 minutes at 72° C.
Final extension: 10 minutes at 72° C.
}

Those that did not display amplification and which therefore carried the integrated plasmid, were selected. The strains with the integrated plasmid were stored in glycerol at −80° C.

Starting from two that were integrated (blue colonies) the excision process was begun, incubating them in liquid medium without antibiotic at 28° C. for 24 hours. In this stage, as a result of a second recombination process, in a percentage of the population there will be excision of the plasmid, with loss of resistance to chloramphenicol and β-galactosidase activity. Dilutions of the culture were seeded on culture plates containing X-gal and sucrose (5%), and the plates were incubated for 24 hours at 28° C.

A number of white colonies (for example 24) were selected and were plated on culture plates with chloramphenicol (20 µg/ml) and on culture plates containing X-gal and sucrose (5%). The chloramphenicol-sensitive colonies were selected and, for these colonies, a PCR was carried out using the oligonucleotides E and F (see FIG. 5) and with the following conditions in the PCR reactions:

30 cycles {
Denaturation: 5 minutes at 94° C.
Denaturation: 45 seconds at 94° C.
Hybridization of the primers: 1 minute at 54° C.
Extension: 3 or 4 minutes at 72° C.
(for rpoS and yeaJ::Km$^R$, respectively)
Final extension: 10 minutes at 72° C.
}

This method was followed, firstly, for producing a deletion in the kanamycin resistance cassette inserted in the gene yeaJ fo strain S. Enteritidis 3934 ΔXII::Km. In this way, the strain S. enteritidis 3934 ΔXII was obtained, wherefrom all of the genes that encode GGDEF proteins are deleted and That, moreover, does not exhibit in its genome any gene able to confer any antibiotic resistance.

Subsequently, S. enteritidis 3934 ΔXII was used to delete gene rpoS. Gene rpoS, as already mentioned, encodes factor sigma 38, a transcription factor that can be used as alternative factor for the initiation of transcription and that regulates transcription of genes involved in the formation of biofilm and the virulence of Salmonella strains. In this way, the strain S. enteritidis 3934 ΔXII ΔrpoS was obtained, which is a strain that lacks all of the genes that encode GGDEF proteins and also lack rpoS factor, which renders the strain incapable of forming biofilm or producing cellulose while maintaining the avirulence of all ΔXII strains. Absence of rpoS factor helps to the stability of all these characteristics.

Absence of the rpoS gene and the kanamycin cassette was also confirmed by PCR using the oligonucleotides E and F, which hybridize in the flanking regions of each of the deleted fragments, and digestion with the restriction enzyme XhoI. The size of the DNA fragments resulting from the amplification reaction and digestion with XhoI for each gene are indicated in Tables 4 and 5.

Strain ΔXII ΔrpoS: Summary of Characterizing Features
Strain: *Salmonella Enteritidis* 3934 ΔXII ΔrpoS
Genotype: *Salmonella enterica* subsp. *Enterica* serovar Enteritidis 3934 Δstm0385 Δstm1283 Δstm1703 Δstm1987 Δstm2123 Δstm2410 Δstm2672 Δstm3375 Δstm3388 Δstm3615 Δstm4551 Δstm2503 ΔrpoS
Antibiotic resistance: None
Scientific description: All of 12 genes that codes for proteins with GGDEF domain and the gene encoding factor sigma 38 (RpoS) deleted from the parental strain *Salmonella enterica* subsp. *Enterica* serovar Enteritidis 3934 (*Salmonella Enteritidis* 3934). The deleted genes are as follows:

stm0385 (adrA, yaiC)
stm1283 (yeaJ)
stm1703 (yciR)
stm1987
stm2123 (yegE)
stm2410 (yfeA)
stm2672 (yfiN)
stm3375 (yhdA)
stm3388
stm3615 (yhjK)
stm4551
stm2503
stm2924 (rpoS)

For each of these genes, except for gen stm1283 (yeaJ), the region encompassing from nucleotide −6 before the first coding codon to nucleotide +6 behind the stop codon has been deleted, introducing an XhoI recognition sequence instead.

Gen stm1283 (yeaJ) was deleted from nucleotide +21 behind the first coding codon to nucleotide +6 behind the stop codon, introducing an XhoI recognition sequence instead.

Absence of all these genes can be confirmed by PCR using the corresponding oligonucleotides E and F, which hybridize in the flanking regions of each of the deleted fragments, and comparing the size of the DNA fragments resulting from the parental strain *Salmonella Enteritidis* 3934 with those resulting from the mutant strain *Salmonella Enteritidis* 3934 ΔXII ΔrpoS (see Table 6). Digestion of the PCR products with the restriction enzyme XhoI can also be carried out (see Table 6 for the size of the resulting DNA fragments).

DEPOSIT OF MICROORGANISMS

The strains *S. enteritidis* 3934 ΔXII::Clo, *S. enteritidis* 3934 ΔXII::Km, *S. enteritidis* 3934 ΔXII+stm1987, *S. enteritidis* 3934 ΔXII+stm4551, *S. enteritidis* 3934 ΔXII ΔrpoS and the *Escherichia coli* strain XL1Blue containing the plasmid pKO3blue were deposited in the Spanish Type Culture Collection (Burjassot, Valencia, Spain) following the rules of the Treaty of Budapest for the deposit of microorganisms for purposes of patents on the following dates and they were assigned the following accession numbers:

| Material | Date of Deposit | Accession number |
| --- | --- | --- |
| *S. enteritidis* 3934 ΔXII::Clo | 27 Feb. 2007 | CECT 7238 |
| *S. enteritidis* 3934 ΔXII::Km | 27 Feb. 2007 | CECT 7237 |
| *S. enteritidis* 3934 ΔXII + stm1987 | 27 Feb. 2007 | CECT 7239 |
| *S. enteritidis* 3934 ΔXII + stm4551 | 27 Feb. 2007 | CECT 7240 |
| *Escherichia coli* XL1Blue pKO3blue | 27 Feb. 2007 | CECT 7241 |
| *S. enteritidis* 3934 ΔXII ΔXII ΔrpoS | 12 May 2010 | CECT 7728 |

The present invention is not limited to the scope of the microorganisms deposited in the patent, since these represent an individual illustration of one aspect of the invention. Any microorganism or plasmid that is functionally equivalent to those described in the invention is included within the invention.

BIBLIOGRAPHIC REFERENCES

Arnaud, M., A. Chastanet & M. Débarbouillé, (2004) A new vector for efficient allelic replacement in naturally non

TABLE 6

Oligonucleotides E and F used and size of the fragments obtained by amplifying the GGDEF genes and the rpoS genes in *S. Enteritidis* 3934 and *S. Enteritidis* 3934 ΔXII ΔrpoS and, optionally, after digesting with XhoI the amplified fragments

| Genome ID | Name of the gene | Oligonucleotides E F | Size of the PCR product: wild-type strain/ mutant XII | Size of the products of digestion of the PCR product of the mutant XII with the enzyme XhoI |
| --- | --- | --- | --- | --- |
| STM0385 | adrA | 01-E (SEQ ID NO: 5) 01-F (SEQ ID NO: 6) | 2427 pb/1310 pb | 745 pb/565 pb |
| STM1283 | yeaJ | 02-E (SEQ ID NO: 101), 02-F (SEQ ID NO: 112) | 2817 pb/1343 pb | 743 pb/600 pb |
| STM1703 | yciR | 03-E (SEQ ID NO: 17) 03-F (SEQ ID NO: 18) | 3375 pb/1386 pb | 711 pb/675 pb |
| STM1987 | | 04-E (SEQ ID NO: 23) 04-F (SEQ ID NO: 24) | 2998 pb/1279 pb | 716 pb/563 pb |
| STM2123 | yegE | 05-E (SEQ ID NO: 29) 05-F (SEQ ID NO: 30) | 4317 pb/1320 pb | 722 pb/598 pb |
| STM2410 | yfeA | 06-E (SEQ ID NO: 35) 06-F (SEQ ID NO: 36) | 3520 pb/1324 pb | 715 pb/609 pb |
| STM2672 | yfiN | 07-E (SEQ ID NO: 43) 07-F (SEQ ID NO: 44) | 2602 pb/1375 pb | 717 pb/658 pb |
| STM3375 | yhdA | 08-E (SEQ ID NO: 49) 08-F (SEQ ID NO: 50) | 3281 pb/1334 pb | 717 pb/617 pb |
| STM3388 | | 09-E (SEQ ID NO: 55) 09-F (SEQ ID NO: 56) | 3448 pb/1342 pb | 730 pb/612 pb |
| STM3615 | yhjK | 10-E (SEQ ID NO: 61) 10-F (SEQ ID NO: 62) | 3378 pb/1398 pb | 709 pb/689 pb |
| STM4551 | | 11-E (SEQ ID NO: 67) 11-F (SEQ ID NO: 68) | 2468 pb/1398 pb | 717 pb/681 pb |
| STM2503 | | 12-E (SEQ ID NO: 73) 12-F (SEQ ID NO: 74) | 3519 pb/1300 pb | 717 pb/583 pb |
| STM2924 | rpoS | rpoS-E (SEQ ID NO: 113) rpoS-F (SEQ ID NO: 114) | 2642 pb/1643 pb | 983 pb/660 pb | transformable low GC % Gram-positive bacteria. *Appl Environ Microbiol* 70: 6887-6891.

Ausubel, F. M., R. Brent, R. E. Kingston, D. D. Moore, J. G. Seidman, J. A. Smith & K. Struhl, (1990) Current protocols in molecular biology. In. New York: John Wiley & Sons, pp.

Ayres, E. K., V. J. Thomson, G. Merino, D. Balderes & D. H. Figurski, (1993) Precise deletions in large bacterial genomes by vector-mediated excision (VEX). The trfA gene of promiscuous plasmid RK2 is essential for replication in several gram-negative hosts. *J Mol Biol* 230: 174-185.

Bitan-Banin, G., R. Ortenberg & M. Mevarech, (2003) Development of a gene knockout system for the halophilic archaeon *Haloferax volcanii* by use of the pyrE gene. *J Bacteriol* 185: 772-778.

Camilli, A., D. T. Beattie & J. J. Mekalanos, (1994) Use of genetic recombination as a reporter of gene expression. *Proc Natl Acad Sci U S A* 91: 2634-2638.

Cherepanov, P. P. & W. Wackernagel, (1995) Gene disruption in *Escherichia coli*: TcR and KmR cassettes with the option of Flp-catalyzed excision of the antibiotic-resistance determinant. *Gene* 158: 9-14.

Christensen, G. D., (1987) The coagulase-negative staphylococci: little brother grows up. *J Am Geriatr Soc* 35: 469-471.

Datsenko, K. A. & B. L. Wanner, (2000) One-step inactivation of chromosomal genes in *Escherichia coli* K-12 using PCR products. *Proc Natl Acad Sci U S A* 97: 6640-6645.

Fabret, C., S. D. Ehrlich & P. Noirot, (2002) A new mutation delivery system for genome-scale approaches in *Bacillus subtilis*. *Mol Microbiol* 46: 25-36.

Galperin, M. Y., (2004) Bacterial signal transduction network in a genomic perspective. *Environ Microbiol* 6: 552-567.

Garcia, B., C. Latasa, C. Solano, F. G. Portillo, C. Gamazo & I. Lasa, (2004) Role of the GGDEF protein family in *Salmonella* cellulose biosynthesis and biofilm formation. *Mol Microbiol* 54: 264-277.

Griffith, K. L. & R. E. Wolf, Jr., (2002) Measuring beta-galactosidase activity in bacteria: cell growth, permeabilization, and enzyme assays in 96-well arrays. *Biochem Biophys Res Commun* 290: 397-402.

Jenal, U. & J. Malone, (2006) Mechanisms of Cyclic-di-GMP Signaling in Bacteria. *Annu Rev Genet*.

Kader, A., R. Simm, U. Gerstel, M. Morr & U. Romling, (2006) Hierarchical involvement of various GGDEF domain proteins in rdar morphotype development of *Salmonella enterica* serovar *Typhimurium*. *Mol Microbiol* 60: 602-616.

Kristensen, C. S., L. Eberl, J. M. Sanchez-Romero, M. Givskov, S. Molin & V. De Lorenzo, (1995) Site-specific deletions of chromosomally located DNA segments with the multimer resolution system of broad-host-range plasmid RP4. *J Bacteriol* 177: 52-58.

Leenhouts, K., G. Buist, A. Bolhuis, A. ten Berge, J. Kiel, I. Mierau, M. Dabrowska, G. Venema & J. Kok, (1996) A general system for generating unlabelled gene replacements in bacterial chromosomes. *Mol Gen Genet*. 253: 217-224.

Link, A. J., D. Phillips & G. M. Church, (1997) Methods for generating precise deletions and insertions in the genome of wild-type *Escherichia coli*: application to open reading frame characterization. *J Bacteriol* 179: 6228-6237.

Maloy, S. R. & W. D. Nunn, (1981) Selection for loss of tetracycline resistance by *Escherichia coli*. *J Bacteriol* 145: 1110-1111.

Maloy, S. R., V. J. Stewart & R. K. Taylor, (1996) *Genetic analysis of pathogenic bacteria: a laboratory manual*. Cold Spring Harbor, N.Y.

Parsell, D. A., A. S. Kowal, M. A. Singer & S. Lindquist, (1994) Protein disaggregation mediated by heat-shock protein Hsp104. *Nature* 372: 475-478.

Peck, R. F., S. Dassarma & M. P. Krebs, (2000) Homologous gene knockout in the archaeon *Halobacterium salinarum* with ura3 as a counterselectable marker. *Mol Microbiol* 35: 667-676.

Ried, J. L. & A. Collmer, (1987) An nptI-sacB-sacR cartridge for constructing directed, unmarked mutations in gram-negative bacteria by marker exchange-eviction mutagenesis. *Gene* 57: 239-246.

Romling, U., M. Gomelsky & M. Y. Galperin, (2005) C-di-GMP: the dawning of a novel bacterial signalling system. *Mol Microbiol* 57: 629-639.

Romling, U., M. Rohde, A. Olsen, S, Normark & J. Reinkoster, (2000) AgfD, the checkpoint of multicellular and aggregative behaviour in *Salmonella typhimurium* regulates at least two independent pathways. *Mol Microbiol* 36: 10-23.

Ryan, R. P., Y. Fouhy, J. F. Lucey & J. M. Dow, (2006) Cyclic Di-GMP Signaling in Bacteria: Recent Advances and New Puzzles. *J Bacteriol* 188: 8327-8334.

Simm, R., M. Morr, A. Kader, M. Nimtz & U. Romling, (2004) GGDEF and EAL domains inversely regulate cyclic di-GMP levels and transition from sessility to motility. Mol Microbiol 53: 1123-1134.

Tal, R., H. C. Wong, R. Calhoon, D. Gelfand, A. L. Fear, G. Volman, R. Mayer, P. Ross, D. Amikam, H. Weinhouse, A. Cohen, S. Sapir, P. Ohana & M. Benziman, (1998) Three cdg operons control cellular turnover of cyclic di-GMP in *Acetobacter xylinum*: genetic organization and occurrence of conserved domains in isoenzymes. *J Bacteriol* 180: 4416-4425.

Tamayo, R., J. T. Pratt & A. Camilli, (2007) Roles of Cyclic Diguanylate in the Regulation of Bacterial Pathogenesis. *Annu Rev Microbiol*.

---

What is claimed is:

1. An isolated mutant strain of *Salmonella enterica* selected from the group consisting of (a) a mutant strain of *Enteritidis* serotype of *Salmonella enterica* designated ΔXII ΔrpoS and deposited in the Spanish Type Culture Collection with accession number CECT 7728, (b) a mutant strain of *Enteritidis* serotype of *Salmonella enterica* designated ΔXII::Km and deposited in the Spanish Type Culture Collection with accession number CECT 7237, and (c) a mutant strain of *Enteritidis* serotype of *Salmonella enterica* designated ΔXII::Clo and deposited in the Spanish Type Culture Collection with accession number CECT 7738.

2. The isolated mutant strain of claim 1, which is the mutant strain of *Enteritidis* serotype of *Salmonella enterica* designated ΔXII ΔrpoS and deposited in the Spanish Type Culture Collection with accession number CECT 7728.

3. The isolated mutant strain of claim 1, which is the mutant strain of *Enteritidis* serotype of *Salmonella enterica* designated ΔXII:Km and deposited in the Spanish Type Culture Collection with accession number CECT 7237.

4. The isolated mutant strain of claim 1, which is the mutant strain of *Enteritidis* serotype of *Salmonella enterica* designated ΔXII::Clo and deposited in the Spanish Type Culture Collection with accession number CECT 7738.

5. A method for vaccination which comprises administration to a mammal of the isolated mutant strain according to claim 1.

6. The method according to claim 5, wherein the animal is a chicken, or a human or other mammal.

7. A method for vaccination which comprises administration to an animal of a medicinal product comprising the isolated mutant strain of claim 2.

* * * * *